US012709600B2

(12) United States Patent
Li et al.

(10) Patent No.: US 12,709,600 B2

(45) Date of Patent: Aug. 18, 2026

(54) BENZONITRIC HETEROCYCLIC COMPOUND, PREPARATION METHOD THEREFOR AND USE THEREOF

(71) Applicants: SHANGHAI ZHONGZE THERAPEUTICS, CO. LTD., Shanghai (CN); SHANGHAI INSTITUTE OF PHARMACEUTICAL INDUSTRY, Shanghai (CN)

(72) Inventors: Jianqi Li, Shanghai (CN); Zheng Guo, Shanghai (CN); Qingwei Zhang, Shanghai (CN); Qiang Pu, Shanghai (CN); Zixue Zhang, Shanghai (CN); Minru Jiao, Shanghai (CN)

(73) Assignees: SHANGHAI ZHONGZE THERAPEUTICS, CO. LTD., Shanghai (CN); SHANGHAI INSTITUTE OF PHARMACEUTICAL INDUSTRY, Shanghai (CN)

( * ) Notice: Subject to any disclaimer, the term of this patent is extended or adjusted under 35 U.S.C. 154(b) by 792 days.

(21) Appl. No.: 17/919,190

(22) PCT Filed: Apr. 14, 2021

(86) PCT No.: PCT/CN2021/087153

§ 371 (c)(1),
(2) Date: Oct. 14, 2022

(87) PCT Pub. No.: WO2021/208945

PCT Pub. Date: Oct. 21, 2021

(65) Prior Publication Data

US 2023/0159463 A1 May 25, 2023

(30) Foreign Application Priority Data

Apr. 17, 2020 (CN) ......................... 202010304883.0

(51) Int. Cl.

*C07D 225/06* (2006.01)
*C07D 267/14* (2006.01)
*C07D 281/10* (2006.01)

(52) U.S. Cl.

CPC ......... *C07D 225/06* (2013.01); *C07D 267/14* (2013.01); *C07D 281/10* (2013.01)

(58) Field of Classification Search

None

See application file for complete search history.

(56) References Cited

U.S. PATENT DOCUMENTS

2011/0288070 A1 11/2011 Rogers et al.

FOREIGN PATENT DOCUMENTS

| | | | |
|---|---|---|---|
| CN | 101573333 | A | 11/2009 |
| CN | 101918389 | A | 12/2010 |
| CN | 102850236 | A | 1/2013 |
| CN | 113527206 | A | 10/2021 |
| TW | 1613198 | B | 2/2018 |
| WO | 2009137462 | A2 | 11/2009 |
| WO | 2017/214359 | A1 | 12/2017 |
| WO | 2018/200608 | A1 | 11/2018 |
| WO | 2019/082910 | A1 | 5/2019 |

OTHER PUBLICATIONS

"Prevention—Prostate Cancer Foundation (PCF)", http://www.pcf.org/site/c.leJRIROrEpH/b.5802029/k.31EA/Prevention.htm, accessed Apr. 18, 2016 (Year: 2016).*

Prichard. British Journal of Surgery, 2003, 90, 772-783 (Year: 2003).*

Marsoni. Epigenetics, 2008, 3:3, 164-171 (Year: 2008).*

Frew. Cancer Letters, 2009, 280, 125-133 (Year: 2009).*

Sleiman. Expert Opinion on Investigational Drugs, 2009, 18:5, 573-584 (Year: 2009).*

Xu. Oxidative Medicine and Cellular Longevity, 2011, article ID 143269, pp. 1-5 (Year: 2011).*

Extended European search report dated Apr. 22, 2024 issued in European Patent Application No. 21789479.9.

First Office Action dated Jan. 21, 2025 issued in Japanese Patent Application No. 2022-562991.

Shen S, et al. Tetrahydroquinoline-Capped Histone Deacetylase 6 Inhibitor SW-101 Ameliorates Pathological Phenotypes in a Charcot-Marie-Tooth Type 2A Mouse Model. J Med Chem. 2021;64(8)4810-4840.

Search Report dated Jun. 30, 2021 issued in International Application No. PCT/CN2021/087153.

Written Opinion dated Jun. 30, 2021 issued in International Application No. PCT/CN2021/087153.

(Continued)

*Primary Examiner* — Noble E Jarrell

(74) *Attorney, Agent, or Firm* — Nath, Goldberg & Meyer; Joshua B. Goldberg

(57) ABSTRACT

Disclosed are a benzonitric heterocyclic compound, a preparation method therefor and the use thereof. Provided in the present invention is a benzonitric heterocyclic compound represented by formula I, or a pharmaceutically acceptable salt thereof, which can be used as a histone deacetylase inhibitor, has a selective inhibitory effect on HDAC6, and has characteristics such as a high efficiency, low toxicity and ideal pharmacokinetic properties.

I

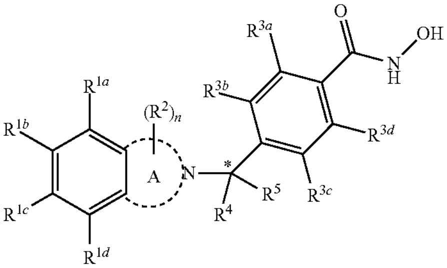

13 Claims, 1 Drawing Sheet

(56) References Cited

OTHER PUBLICATIONS

Office Action dated Jul. 12, 2022 issued in corresponding Chinese Application No. 202010304883.0.
Office Action dated issued Nov. 30, 2022 inin corresponding Taiwanese Application No. 110113353.
Search Report dated Jun. 30, 2020 issued by STN International.
Shidore, et al., "3-Substituted 1-methyl-3-benzazepin-2-ones as 5-HT2C receptor agonists", RSC Adv, vol. 5, pp. 91908-91921, 2015.
Guo, et al., "Design, synthesis and biological evalution of brain penetrant benzazepine-based histone deacetylase 6 inhibitors for alleviating stroke-induced brain infarcton", European Journal of Medicinal Chemistry, vol. 218, 2021.
Lee, et al., "Solid-Phase Synthesis of 3,4,5-Substituted 1,5-Benzodiazepin-2-ones", J. Org. Chem, vol. 64, pp. 3060-3065, 1999.
Butler, et al., "Rational Design and Simple Chemistry Yield a Superior, Neuroprotective HDAC5 Inhibitor, Tubastatin A", JACS Articles, vol. 132, pp. 10842-10846, 2010.
Kozikowski, et al., Brain Penetrable Histone Deacetylase 6 Inhibitor SW-100 Ameliorates Memory and Learning Impairments in a Mouse Model of Fragile X Syndrome, ACS Chemical Neuroscience, Dec. 4, 2018.

* cited by examiner

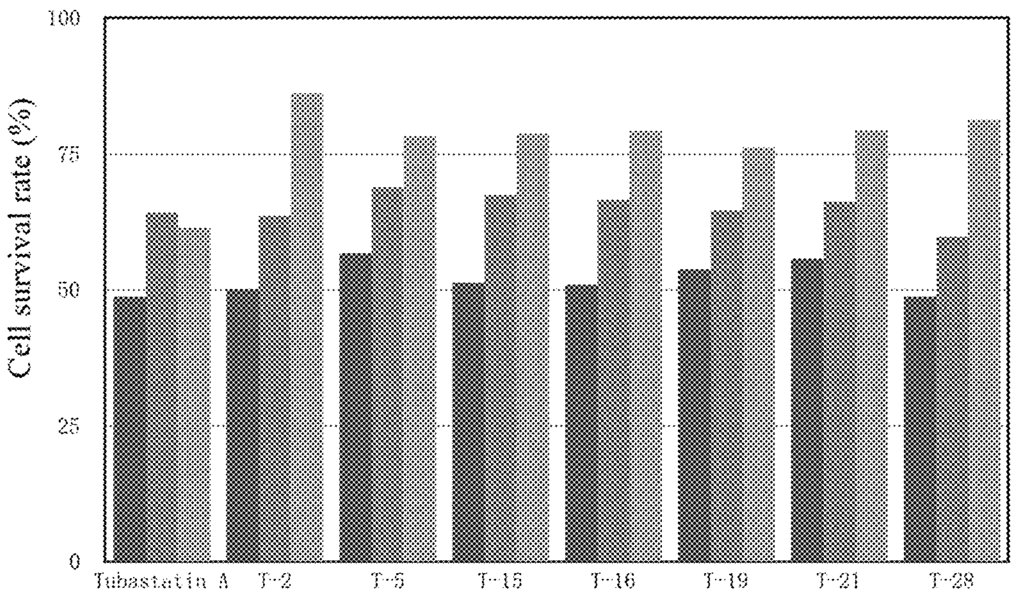
Cell survival rate in the HCA-induced neuronal toxicity model
Cell survival rate (%)
100
75
50
25
0
Tubastatin A
T-2
T-5
T-15
T-16
T-19
T-21
T-28

BENZONITRIC HETEROCYCLIC COMPOUND, PREPARATION METHOD THEREFOR AND USE THEREOF

This is a National Phase Application filed under 35 U.S.C. 371 as a national stage of PCT/CN2021/0087153, filed Apr. 14, 2021, an application claiming the benefit of Chinese Application No. 202010304883.0, filed Apr. 17, 2020, the content of each of which is hereby incorporated by reference in its entirety.

TECHNICAL FIELD

The present disclosure relates to a benzonitric heterocyclic compound, a preparation method therefor and a use thereof.

BACKGROUND

Histone deacetylases (HDACs) can catalyze the deacetylation process of histones and non-histones, and regulate intracellular acetylation level together with histone acetyltransferases (HATs), thereby regulating gene expression. At present, there are 18 subtypes of mammalian HDACs, which can be divided into four classes: class I (HDAC1, HDAC2, HDAC3, HDAC8); class II is further divided into IIa (HDAC4, HDAC5, HDAC7, HDAC9) subfamily and IIb (HDAC6, HDAC10) subfamily; class III (Sirt1-Sirt7); class IV (HDAC11).

There are currently five histone deacetylase inhibitors (HDACi) on the market, vorinostat, belinostat, panobinostat, romidepsin and chidamide, respectively, the first three are broad-spectrum inhibitors, and the latter two selectively act on class I subtypes. Vorinostat and romidepsin are used to treat cutaneous T cell lymphoma (CTCL), belinostat and chidamide are used to treat relapsed and refractory peripheral T-cell lymphoma (PTCL), and panobinostat in combination with bortezomib and dexamethasone are used to treat multiple myeloma (MM).

Although the above HDAC inhibitors have achieved good clinical effects, the broad-spectrum HDAC inhibitors generally have the following disadvantages:

(1) strong toxic side effects, such as nausea, vomiting, bone marrow suppression, etc.;

(2) genotoxicity;

(3) poor pharmacokinetic properties, low bioavailability, short half-life, etc.

The above disadvantages not only cause inconvenience to tumor patients, but also hinder the use of broad-spectrum HDAC inhibitors in fields other than tumor therapy.

At present, HDACs subtype-selective inhibitors have become the research focus in this field, among which HDAC6 subtype inhibitors have attracted much attention. HDAC6 involves a wide range of diseases, including tumor, neurodegenerative diseases, inflammation, autoimmune response, tumor and bacterial infection, etc.

Pharmacological studies have shown that HDAC6 selective inhibitors can effectively inhibit the proliferation of glioblastoma cells and induce their apoptosis, and inhibition of HDAC6 can enhance the sensitivity of glioblastoma cells to temozolomide, suggesting that the two have a synergistic effect. Specifically, HDAC6 can regulate the activity of its acetylation substrates such as heat shock proteins, and the heat shock proteins can be involved in the repair of misfolded and unfolded proteins as molecular chaperones; meanwhile, the ZnF-UBP domain of HDAC6 protein can bind ubiquitinated misfolded proteins with high affinity and promote their degradation. The chaperone p97/VCP of HDAC6 can separate the HDAC6-ubiquitin complex, and the balance between the two can affect the fate of misfolded and unfolded proteins during endoplasmic reticulum stress (ERS) and unfolded protein response of cells (UPR). Thus, combination therapy of the HDAC6 inhibitor Tubastatin A and temozolomide (TMZ) reverse the ratio between HDAC6 and p97/VCP, attenuate Hsp activation, and trigger unfolded protein response and ERS pro-apoptosis signals, and finally overcome ERS toleration, reduce viability of TMZ-resistant glioma cells and induce apoptosis.

Similar to glioma, Alzheimer's disease (AD) is also urgent in need of effective therapeutic drugs in clinical, and studies have found that the expression level of HDAC6 is significantly increased in the hippocampus (increased by 91%) and cortex (increased by 52%) of AD brains and tubulin acetylation is reduced in neurons containing NFTs. HDAC6 is involved in the process of tau hyperphosphorylation. HDAC6 interacts with tau in human brain tissue and this interaction is mediated by the microtubule binding domain on tau and the SE14 domain on HDAC6. HDAC6 inhibition does not affect its interaction with tau, but attenuates T231 phosphorylation of tau, and T231 is a key regulatory site for tau function. HDAC6 inhibition improves cognition in AD mice. The above studies show that centrally-targeted HDAC6 inhibitors are expected to be developed into new high-efficiency and low-toxic AD therapeutic drug.

The literature (*J. Am. Chem. Soc.* 2010, 132, 31, 10842-10846) reported that Tubastatin A, an arylhydroxamic acid HDAC6 inhibitor containing a carbazole structure, had a central neuroprotective effect with poor physicochemical property and poor druggability.

The literature (*ACS Chem. Neurosci.* 2019, 10, 3, 1679-1695) reported that SW-100, a HDAC6 inhibitor ($IC_{50}$=2.3 nM) containing a tetrahydroquinoline structure, had a certain cognitive improvement effect in cognitively impaired mice.

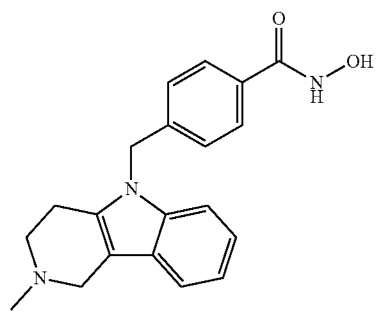

Tubastatin A

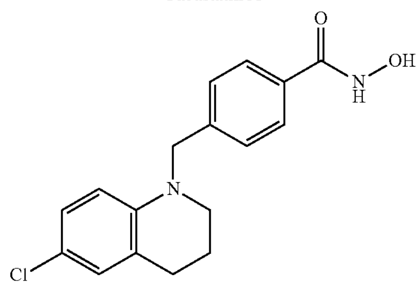

SW-100

Patent WO 2018200608 A disclosed a class of indoline compounds, wherein compound II-ING-39 inhibited HDAC6 with $IC_{50}$=21.5 nM, which was nearly one order of magnitude weaker than SW-100 ($IC_{50}$=2.3 nM), and the substituents of benzene ring in indoline had a greater impact on HDAC6 inhibitory activity, for example, the nitro-substituted compound II-ING-57 had significantly better HDAC6 inhibitory activity ($IC_{50}$=1.4 nM) than II-ING-39 and II-ING-44.

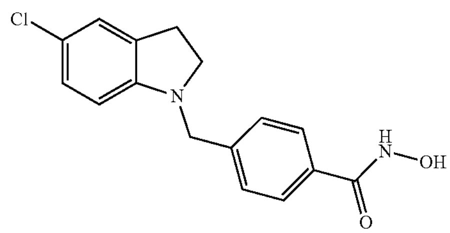

II-ING-39
HDAC6 IC50 = 21.5 nM

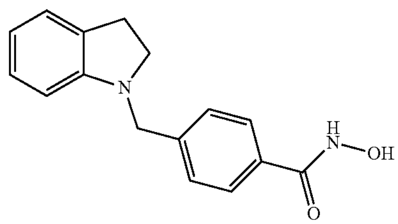

II-ING-44
HDAC6 IC50 = 26.8 nM

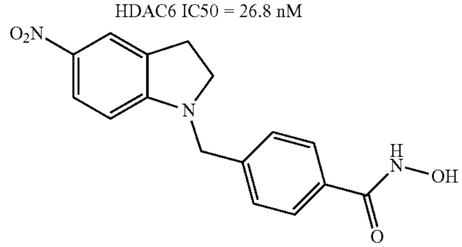

II-ING-57
HDAC IC50 = 1.4 nM

The above disclosed literatures and patents suggest that the different nitric heterocyclic structures and the different substituents on benzene affect the inhibitory activity of compounds on HDAC6, but the influence degree and the produced pharmacological effects are unpredictable and need to be verified by experiments.

CONTENT OF THE PRESENT INVENTION

The technical problem actually solved in the present disclosure is to overcome the defect of single HDAC6 inhibitor, especially poor selectivity in the prior art, and provide a benzonitric heterocyclic compound, a preparation method therefor and a use thereof. Provided in the present disclosure is a benzonitric heterocyclic compound, which can be used as a histone deacetylase inhibitor, has a selective inhibitory effect on HDAC6, and has characteristics such as a high efficiency, low toxicity and ideal pharmacokinetic properties and so on and are expected to meet clinical needs as therapeutic agents for anti-tumor or neurodegenerative disease.

The present disclosure solves the above technical problems by the following technical solution.

The present disclosure provides a benzonitric heterocyclic compound represented by formula I or a pharmaceutically acceptable salt thereof:

I

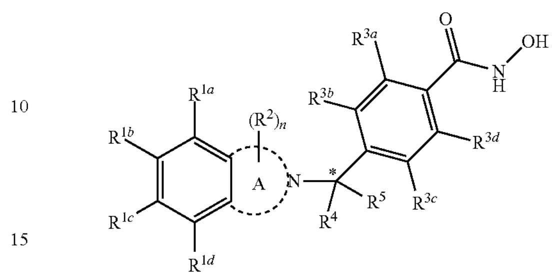

wherein, ring A

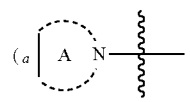

the a side represents the ring fused with the benzene

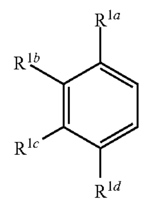

is a 7-membered heterocycloalkyl; in the 7-membered heterocycloalkyl, in addition to the N atom which is connected with the

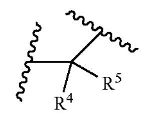

the 7-membered heterocycloalkyl also contains 0 to 2 heteroatoms optionally selected from N, O, S, S(═O) and $S(═O)_2$;

n is 0, 1, 2, 3 or 4;

$R^2$ is independently hydrogen, hydroxyl, $C_1$-$C_4$ alkyl, $C_1$-$C_4$ alkyl-O—, $(R^aR^b)N$— or O═ (when —$CH_2$— is substituted);

$R^{1a}$, $R^{1b}$, $R^{1c}$ and $R^{1d}$ are independently hydrogen, halogen, hydroxyl, cyano or $R^1$-L-;

-L- is independently a linker bond, —($C_1$-$C_4$ alkyl)-, —O—, —C(═O)— or —$S(═O)_2$—;

$R^1$ is independently $C_1$-$C_6$ alkyl, $C_3$-$C_7$ cycloalkyl, $C_6$-$C_{10}$ aryl, $(R^cR^d)N$—, 3- to 7-membered heterocycloalkyl or 5- to 10-membered heteroaryl, or, the $C_1$-$C_6$ alkyl, $C_3$-$C_7$ cycloalkyl, $C_6$-$C_{10}$ aryl, $(R^cR^d)N$—, 3- to 7-membered heterocycloalkyl and 5- to 10-membered heteroaryl are substituted by one or more substituents of $R^e$; in the 3- to 7-membered heterocycloalkyl and the 3- to 7-membered heterocycloalkyl substituted by one or more substituents of $R^e$, the heteroatom is selected from one or more of N, O, S, S(=O) and $S(=O)_2$, and the number of heteroatoms is 1 to 3; in the 5- to 10-membered heteroaryl and the 5- to 10-membered heteroaryl substituted by one or more substituents of $R^e$, the heteroatom is selected from one or more of N, O and S, and the number of heteroatoms is 1 to 4; $R^e$ is independently hydroxyl, halogen, cyano or $C_1$-$C_4$ alkyl; when there are multiple substituents, they are the same or different;

$R^a$, $R^b$, $R^c$ and $R^d$ are independently hydrogen or $C_1$-$C_4$ alkyl;

$R^{3a}$, $R^{3b}$, $R^{3c}$, $R^{3d}$, $R^4$ and $R^5$ are independently hydrogen, halogen, $C_1$-$C_4$ alkyl or $C_1$-$C_4$ alkyl substituted by one or more halogen; when there are multiple substituents, they are the same or different;

a carbon atom with "*" indicates that when it is a chiral carbon atom, it is a S configuration, R configuration or a mixture thereof.

In some preferred embodiments of the present disclosure, some groups in the benzonitric heterocyclic compound represented by formula I are defined as follows (the groups not mentioned are as described in any one of embodiments of the present disclosure), in ring A, the N connected with the

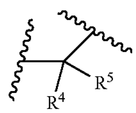

is located at the ortho, meta or para position of the benzene fused with the ring; for example, at the ortho or the para position; for another example, at the ortho position.

In some preferred embodiments of the present disclosure, some groups in the benzonitric heterocyclic compound represented by formula I are defined as follows (the groups not mentioned are as described in any one of embodiments of the present disclosure), in ring A, in addition to the N atom which is connected with the

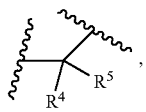, and the ring A also contains 0 to 1 heteroatom optionally selected from N, O and S;

for example,

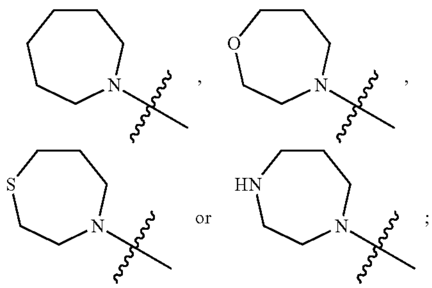

the a side is fused with the benzene.

In some preferred embodiments of the present disclosure, some groups in the benzonitric heterocyclic compound represented by formula I are defined as follows (the groups not mentioned are as described in any one of embodiments of the present disclosure), when $R^2$ is independently $C_1$-$C_4$ alkyl or $C_1$-$C_4$ alkyl-O—, the $C_1$-$C_4$ alkyl in the $C_1$-$C_4$ alkyl and $C_1$-$C_4$ alkyl-O— is methyl, ethyl, n-propyl, isopropyl, n-butyl, isobutyl, sec-butyl or tert-butyl; for example, methyl.

In some preferred embodiments of the present disclosure, some groups in the benzonitric heterocyclic compound represented by formula I are defined as follows (the groups not mentioned are as described in any one of embodiments of the present disclosure), when $R^{1a}$, $R^{1b}$, $R^{1c}$ and $R^{1d}$ are independently halogen, the halogen is fluorine, chlorine, bromine or iodine, for example, fluorine, chlorine or bromine; for another example, fluorine.

In some preferred embodiments of the present disclosure, some groups in the benzonitric heterocyclic compound represented by formula I are defined as follows (the groups not mentioned are as described in any one of embodiments of the present disclosure), when -L- is independently —($C_1$-$C_4$ alkyl)-, the —($C_1$-$C_4$ alkyl)- is methylene, ethylene, propylene, butylene, isopropylidene, isobutylene, sec-butylene or tert-butylene, for example, methylene.

In some preferred embodiments of the present disclosure, some groups in the benzonitric heterocyclic compound represented by formula I are defined as follows (the groups not mentioned are as described in any one of embodiments of the present disclosure), when $R^1$ is independently $C_1$-$C_6$ alkyl, $C_1$-$C_6$ alkyl substituted by one or more substituents of $R^e$, the $C_1$-$C_6$ alkyl in the $C_1$-$C_6$ alkyl and $C_1$-$C_6$ alkyl substituted by one or more substituents of $R^e$ is independently $C_1$-$C_4$ alkyl (for example methyl, ethyl, n-propyl, isopropyl, n-butyl, isobutyl, sec-butyl or tert-butyl), for example, methyl.

In some preferred embodiments of the present disclosure, some groups in the benzonitric heterocyclic compound represented by formula I are defined as follows (the groups not mentioned are as described in any one of embodiments of the present disclosure), when $R^1$ is independently $C_3$-$C_7$ cycloalkyl, $C_3$-$C_7$ cycloalkyl substituted by one or more substituents of $R^e$, the $C_3$-$C_7$ cycloalkyl in the $C_3$-$C_7$ cycloalkyl and $C_3$-$C_7$ cycloalkyl substituted by one or more substituents of $R^e$ is independently cyclopropyl, cyclobutyl, cyclopentyl, cyclohexyl and cycloheptyl; for example, cyclopropyl.

In some preferred embodiment of the present disclosure, some groups in the benzonitric heterocyclic compound represented by formula I are defined as follows (the groups not mentioned are as described in any scheme of the present disclosure), when $R^1$ is independently $C_6$-$C_{10}$ aryl, $C_6$-$C_{10}$ aryl substituted by one or more substituents of $R^e$, the $C_6$-$C_{10}$ aryl in the $C_6$-$C_{10}$ aryl and $C_6$-$C_{10}$ aryl substituted with one or more substituents of $R^e$ is independently phenyl or naphthyl, for example, phenyl.

In some preferred embodiments of the present disclosure, some groups in the benzonitric heterocyclic compound represented by formula I are defined as follows (the groups not mentioned are as described in any one of embodiments of the present disclosure), when $R^1$ is independently 3- to 7-membered heterocycloalkyl and 3- to 7-membered heterocycloalkyl substituted by one or more substituents of $R^e$, the 3- to 7-membered heterocycloalkyl in the 3- to 7-membered heterocycloalkyl and 3- to 7-membered heterocycloalkyl substituted by one or more substituents of $R^e$ is independently 5- to 6-membered heterocycloalkyl, wherein the heteroatom is selected from one or more of N, O and S, and the number of heteroatoms is 1 to 2, for example piperidinyl (for another example,

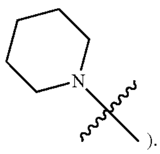 [SMILES: *N1CCCCC1]

).

In some preferred embodiments of the present disclosure, some groups in the benzonitric heterocyclic compound represented by formula I are defined as follows (the groups not mentioned are as described in any one of embodiments of the present disclosure), when $R^1$ is independently 5- to 10-membered heteroaryl and 5- to 10-membered heteroaryl substituted by one or more substituents of $R^e$, the 5- to 10-membered heteroaryl in the 5- to 10-membered heteroaryl and 5- to 10-membered heteroaryl substituted by one or more substituents of $R^e$ is independently 5- to 6-membered heteroaryl, wherein the heteroatom is selected from one or more of N, O and S, and the number of heteroatoms is 1 to 2, for example piperidinyl (for another example,

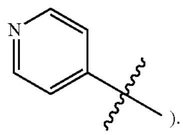

).

In some preferred embodiments of the present disclosure, some groups in the benzonitric heterocyclic compound represented by formula I are defined as follows (the groups not mentioned are as described in any one of embodiments of the present disclosure), when $R^c$ is independently halogen, the halogen is fluorine, chlorine, bromine or iodine, for example fluorine or chlorine.

In some preferred embodiments of the present disclosure, some groups in the benzonitric heterocyclic compound represented by formula I are defined as follows (the groups not mentioned are as described in any one of embodiments of the present disclosure), when $R^e$ is independently $C_1$-$C_4$ alkyl, the $C_1$-$C_4$ alkyl is methyl, ethyl, n-propyl, isopropyl, n-butyl, isobutyl, sec-butyl or tert-butyl; for example, methyl.

In some preferred embodiments of the present disclosure, some groups in the benzonitric heterocyclic compound represented by formula I are defined as follows (the groups not mentioned are as described in any one of embodiments of the present disclosure), when $R^a$, $R^b$, $R^c$ and $R^d$ are independently $C_1$-$C_4$ alkyl, the $C_1$-$C_4$ alkyl is methyl, ethyl, n-propyl, isopropyl, n-butyl, isobutyl, sec-butyl or tert-butyl; for example, methyl.

In some preferred embodiments of the present disclosure, some groups in the benzonitric heterocyclic compound represented by formula I are defined as follows (the groups not mentioned are as described in any one of embodiments of the present disclosure), when $R^{3a}$, $R^{3b}$, $R^{3c}$, $R^{3d}$, $R^4$ and $R^5$ are independently $C_1$-$C_4$ alkyl or $C_1$-$C_4$ alkyl substituted by one or more halogen, the $C_1$-$C_4$ alkyl in the $C_1$-$C_4$ alkyl or $C_1$-$C_4$ alkyl substituted by one or more halogen is methyl, ethyl, n-propyl, isopropyl, n-butyl, isobutyl, sec-butyl or tert-butyl; for example, methyl.

In some preferred embodiments of the present disclosure, some groups in the benzonitric heterocyclic compound represented by formula I are defined as follows (the groups not mentioned are as described in any one of embodiments of the present disclosure), when $R^{3a}$, $R^{3b}$, $R^{3c}$, $R^{3d}$, $R^4$ and $R^5$ are independently halogen or $C_1$-$C_4$ alkyl substituted by one or more halogen, the halogen in the halogen or $C_1$-$C_4$ alkyl substituted by one or more halogen is fluorine, chlorine, bromine or iodine, for example, fluorine or chlorine.

In some preferred embodiments of the present disclosure, some groups in the benzonitric heterocyclic compound represented by formula I are defined as follows (the groups not mentioned are as described in any one of embodiments of the present disclosure), when $R^1$ is independently $C_1$-$C_6$ alkyl, $C_3$-$C_7$ cycloalkyl, $C_6$-$C_{10}$ aryl, $(R^cR^d)N$—, 3- to 7-membered heterocycloalkyl or 5- to 10-membered heteroaryl, and the $C_1$-$C_6$ alkyl, $C_3$-$C_7$ cycloalkyl, $C_6$-$C_{10}$ aryl, $(R^cR^d)N$—, 3- to 7-membered heterocycloalkyl and 5- to 10-membered heteroaryl are substituted by substituents of $R^e$, and the $R^e$ is independently halogen, and the number of $R^e$ is 1, 2 or 3;

for example, trifluoromethyl.

In some preferred embodiments of the present disclosure, some groups in the benzonitric heterocyclic compound represented by formula I are defined as follows (the groups not mentioned are as described in any one of embodiments of the present disclosure), when $R^{3a}$, $R^{3b}$, $R^{3c}$, $R^{3d}$, $R^4$ and $R^5$ are independently $C_1$-$C_4$ alkyl substituted by one or more halogen, the number of halogen substitutions is substituted by 1 to 3 halogens, for example, trifluoromethyl.

In some preferred embodiments of the present disclosure, some groups in the benzonitric heterocyclic compound represented by formula I are defined as follows (the groups not mentioned are as described in any one of embodiments of the present disclosure), ring A is

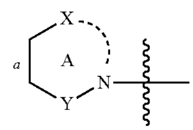

;

Y is a linker bond, methylene or ethylene ( 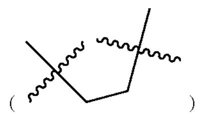 [SMILES: *CC*] )

(i.e., ring A is

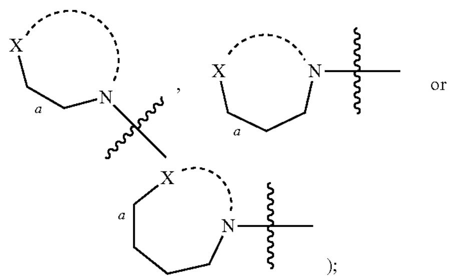 );

for example, Y is a linker bond or

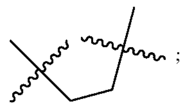 [SMILES: *CC*] ;

X is C, N, O or S; the a side is fused with the benzene.

In some preferred embodiments of the present disclosure, some groups in the benzonitric heterocyclic compound represented by formula I are defined as follows (the groups not mentioned are as described in any one of embodiments of the present disclosure), n is 0 or 1.

In some preferred embodiments of the present disclosure, some groups in the benzonitric heterocyclic compound represented by formula I are defined as follows (the groups not mentioned are as described in any one of embodiments of the present disclosure), $R^2$ is independently hydrogen, hydroxyl, $C_1$-$C_4$ alkyl, $(R^aR^b)N$— or O═;

for example, hydrogen, hydroxyl, $C_1$-$C_4$ alkyl or O═.

In some preferred embodiments of the present disclosure, some groups in the benzonitric heterocyclic compound represented by formula I are defined as follows (the groups not mentioned are as described in any one of embodiments of the present disclosure), -L- is independently a linker bond or —O—.

In some preferred embodiments of the present disclosure, some groups in the benzonitric heterocyclic compound represented by formula I are defined as follows (the groups not mentioned are as described in any one of embodiments of the present disclosure), $R^1$ is independently $C_1$-$C_6$ alkyl, $C_3$-$C_7$ cycloalkyl, $C_6$-$C_{10}$ aryl, $(R^cR^d)N$—, 3- to 7-membered heterocycloalkyl, or 5- to 10-membered heteroaryl; for example, $C_1$-$C_6$ alkyl.

In some preferred embodiments of the present disclosure, some groups in the benzonitric heterocyclic compound represented by formula I are defined as follows (the groups not mentioned are as described in any one of embodiments of the present disclosure), $R^1$-L- is $C_3$-$C_7$ cycloalkyl, $C_6$-$C_{10}$ aryl, $(R^cR^d)N$—, 3- to 7-membered heterocycloalkyl, 5- to 10-membered heteroaryl or $C_1$-$C_6$ alkyl-O—; for example, $C_1$-$C_6$ alkyl-O—.

In some preferred embodiments of the present disclosure, some groups in the benzonitric heterocyclic compound represented by formula I are defined as follows (the groups not mentioned are as described in any one of embodiments of the present disclosure), $R^{1a}$, $R^{1b}$, $R^{1c}$ and $R^{1d}$ are independently hydrogen, halogen or $R^1$-L-;

for example, one or two of $R^{1a}$, $R^{1b}$, $R^{1c}$ and $R^{1d}$ are independently halogen or $R^1$-L-; and the rest are hydrogen;

for another example, one or two of $R^{1a}$, $R^{1b}$, $R^{1c}$ and $R^{1d}$ are independently $C_1$-$C_6$ alkyl-O—; and the rest are hydrogen; or, $R^{1c}$ is halogen, and the rest are hydrogen; the halogen is preferably fluorine.

In some preferred embodiments of the present disclosure, some groups in the benzonitric heterocyclic compound represented by formula I are defined as follows (the groups not mentioned are as described in any one of embodiments of the present disclosure), $R^4$ and $R^5$ are independently hydrogen or halogen; for example, hydrogen.

In some preferred embodiments of the present disclosure, some groups in the benzonitric heterocyclic compound represented by formula I are defined as follows (the groups not mentioned are as described in any one of embodiments of the present disclosure), $R^a$, $R^b$, $R^c$ and $R^d$ are independently $C_1$-$C_4$ alkyl.

In some preferred embodiments of the present disclosure, some groups in the benzonitric heterocyclic compound represented by formula I are defined as follows (the groups not mentioned are as described in any one of embodiments of the present disclosure), $R^{3a}$, $R^{3b}$, $R^{3c}$ and $R^{3d}$ are independently hydrogen or halogen; for example, hydrogen;

for example, $R^{3a}$ and $R^{3d}$ are independently hydrogen or halogen; $R^{3b}$ and $R^{3c}$ are independently hydrogen;

for another example, $R^{3a}$ is hydrogen or halogen; $R^{3b}$, $R^{3c}$ and $R^{3d}$ are independently hydrogen.

In some preferred embodiments of the present disclosure, some groups in the benzonitric heterocyclic compound represented by formula I are defined as follows (the groups not mentioned are as described in any one of embodiments of the present disclosure), the benzoazepine compound represented by formula I is a benzonitric heterocyclic compound represented by formula I-1 or formula I-2:

I-1

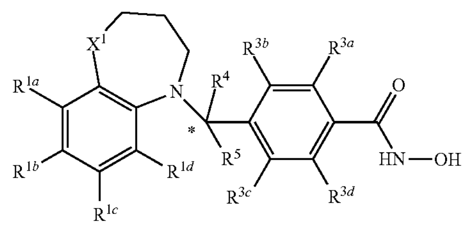

-continued

I-2

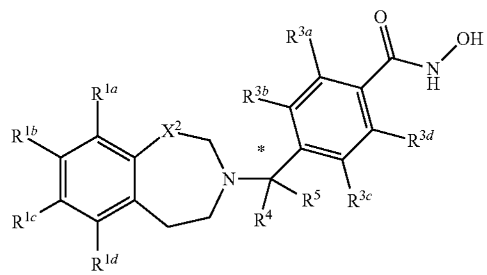

wherein, $X_1$ and $X_2$ are independently

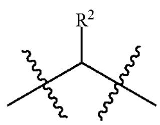

(when $R^2$ is =O,

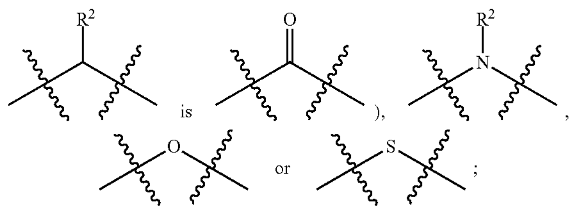

preferably, the benzonitric heterocyclic compound is represented by formula I-1.

In some preferred embodiments of the present disclosure, some groups in the benzonitric heterocyclic compound represented by formula I are defined as follows (the groups not mentioned are as described in any one of embodiments of the present disclosure), ring A is 7-membered heterocycloalkyl;

in ring A, the N connected with the

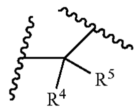

is located at the ortho or para position of the benzene; for another example, at the ortho position;

n is 0 or 1;

$R^2$ is independently hydrogen, hydroxyl, $C_1$-$C_4$ alkyl, $C_1$-$C_4$ alkyl-O—, $(R^aR^b)N$— or O=; for example, hydrogen, hydroxyl, $C_1$-$C_4$ alkyl, $(R^aR^b)N$— or O=; for another example, hydrogen, hydroxyl, $C_1$-$C_4$ alkyl, or O=;

$R^{1a}$, $R^{1b}$, $R^{1c}$ and $R^{1d}$ are independently hydrogen, halogen or $R^1$-L-;

-L- is independently a linker bond or —O—;

$R^1$ is independently $C_1$-$C_6$ alkyl, $C_3$-$C_7$ cycloalkyl, $C_6$-$C_{10}$ aryl, $(R^cR^d)N$—, 3- to 7-membered heterocycloalkyl, or 5- to 10-membered heteroaryl;

$R^4$ and $R^5$ are independently hydrogen or halogen;

$R^{3a}$, $R^{3b}$, $R^{3c}$ and $R^{3d}$ are independently hydrogen or halogen;

preferably, $R^1$-L- is $C_1$-$C_6$ alkyl-O—, $C_3$-$C_7$ cycloalkyl, $C_6$-$C_{10}$ aryl, $C_6$-$C_{10}$ aryl-($C_1$-$C_4$ alkyl)-, $(R^cR^d)N$—, 3- to 7-membered heterocycloalkyl or 5- to 10-membered heteroaryl.

In some preferred embodiments of the present disclosure, some groups in the benzonitric heterocyclic compound represented by formula I are defined as follows (the groups not mentioned are as described in any one of embodiments of the present disclosure), ring A is

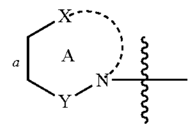

Y is a linker bond or

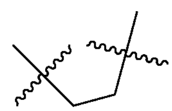

X is C, N, O or S;

n is 0 or 1;

$R^2$ is independently hydrogen, hydroxyl, $C_1$-$C_4$ alkyl, $C_1$-$C_4$ alkyl-O—, $(R^aR^b)N$— or O=; for example, hydrogen, hydroxyl, $C_1$-$C_4$ alkyl, $(R^aR^b)N$— or O=; for another example, hydrogen, hydroxyl, $C_1$-$C_4$ alkyl, or O=;

$R^{1a}$, $R^{1b}$, $R^{1c}$ and $R^{1d}$ are independently hydrogen, halogen, $C_1$-$C_6$ alkyl-O—, $C_3$-$C_7$ cycloalkyl, $C_6$-$C_{10}$ aryl, $C_6$-$C_{10}$ aryl-($C_1$-$C_4$ alkyl)-, $(R^cR^d)N$—, 3- to 7-membered heterocycloalkyl or 5- to 10-membered heteroaryl; for example, hydrogen, fluorine or $C_1$-$C_6$ alkyl-O—;

$R^4$ and $R^5$ are independently hydrogen;

$R^{3a}$, $R^{3b}$, $R^{3c}$ and $R^{3d}$ are independently hydrogen or halogen; for example, $R^{3a}$ and $R^{3d}$ are independently hydrogen or halogen; $R^{3b}$ and $R^{3c}$ are independently hydrogen; for another example, $R^{3a}$ is hydrogen or halogen; $R^{3b}$, $R^{3c}$ and $R^{3d}$ are independently hydrogen.

In some preferred embodiments of the present disclosure, some groups in the benzonitric heterocyclic compound represented by formula I are defined as follows (the groups not mentioned are as described in any one of embodiments of the present disclosure), ring A is

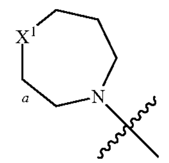

$X^1$ is independently

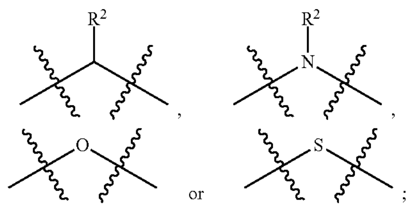

n is 0 or 1;

$R^2$ is independently hydrogen, hydroxyl, $C_1$-$C_4$ alkyl or O═;

$R^{1a}$, $R^{1b}$, $R^{1c}$ and $R^{1d}$ are independently hydrogen, fluorine or $C_1$-$C_6$ alkyl-O—; for example, one or two of $R^{1a}$, $R^{1b}$, $R^{1c}$ and $R^{1d}$ are independently fluorine or $C_1$-$C_6$ alkyl-O—, the rest are hydrogen;

for another example, one or two of $R^{1a}$, $R^{1b}$, $R^{1c}$ and $R^{1d}$ are independently $C_1$-$C_6$ alkyl-O—; and the rest are hydrogen; or, $R^{1c}$ is fluorine, and the rest are hydrogen;

$R^{3a}$, $R^{3b}$, $R^{3c}$, $R^{3d}$, $R^4$ and $R^5$ are independently hydrogen.

In some preferred embodiments of the present disclosure, some groups in the benzonitric heterocyclic compound represented by formula I are defined as follows (the groups not mentioned are as described in any one of embodiments of the present disclosure), ring A is

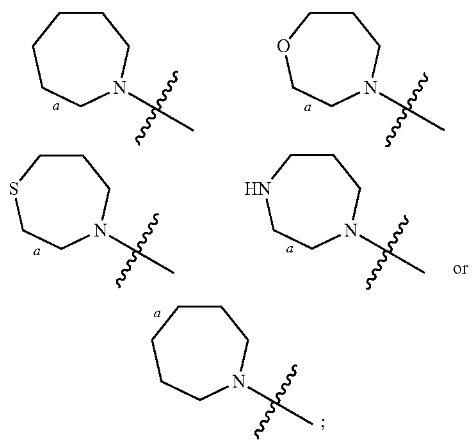

the a side is fused with the benzene.

In some preferred embodiments of the present disclosure, some groups in the benzonitric heterocyclic compound represented by formula I are defined as follows (the groups not mentioned are as described in any one of embodiments of the present disclosure), $R^{1a}$, $R^{1b}$, $R^{1c}$ and $R^{1d}$ are independently hydrogen, fluorine, chlorine, bromine, methoxy, cyclopropyl, phenyl,

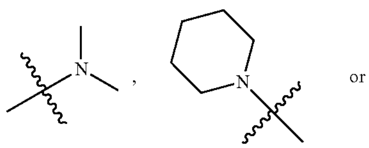

-continued

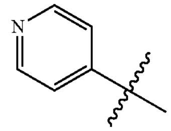

for example, hydrogen, fluorine, methoxy.

In some preferred embodiments of the present disclosure, some groups in the benzonitric heterocyclic compound represented by formula I are defined as follows (the groups not mentioned are as described in any one of embodiments of the present disclosure), $R^2$ is independently hydrogen, hydroxyl, methyl, methoxy,

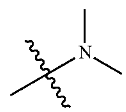 [SMILES: *N(C)C]

or O═.

In some preferred embodiments of the present disclosure, some groups in the benzonitric heterocyclic compound represented by formula I are defined as follows (the groups not mentioned are as described in any one of embodiments of the present disclosure), $R^4$ and $R^5$ are independently hydrogen or fluorine; for example, hydrogen.

In some preferred embodiments of the present disclosure, some groups in the benzonitric heterocyclic compound represented by formula I are defined as follows (the groups not mentioned are as described in any one of embodiments of the present disclosure), $R^{3a}$, $R^{3b}$, $R^{3c}$ and $R^{3d}$ are independently hydrogen or fluorine;

for example, $R^{3a}$, $R^{3b}$, $R^{3c}$ and $R^{3d}$ are independently hydrogen.

In a certain embodiment of the present disclosure, the benzonitric heterocyclic compound represented by formula I is selected from any of the following structures:

T-1

T-2

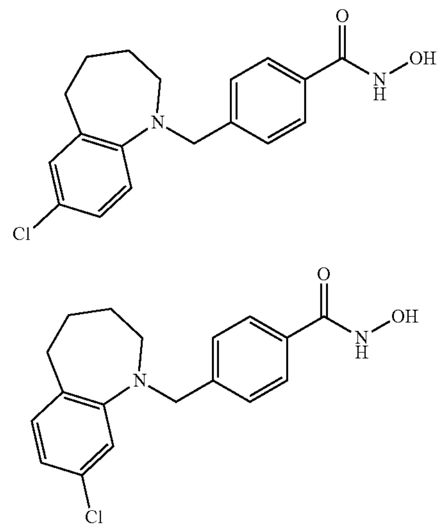

-continued
T-3
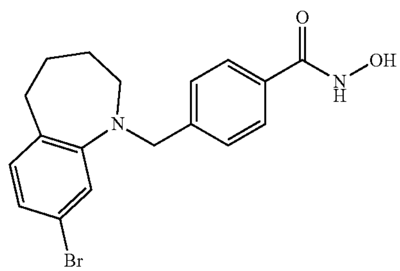
T-4
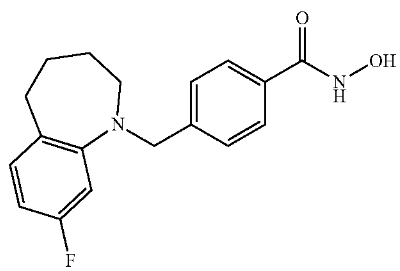
T-5
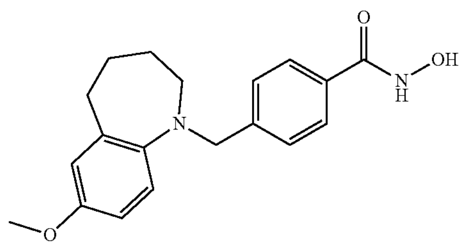
T-6
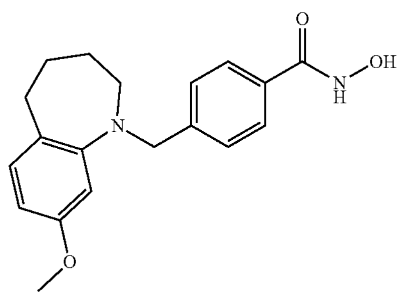
T-7
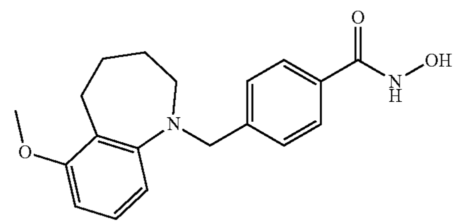
T-8
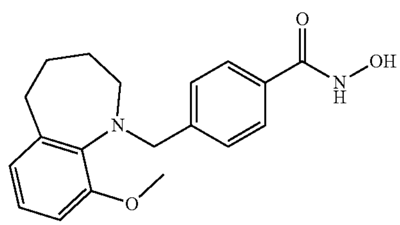
-continued
T-9
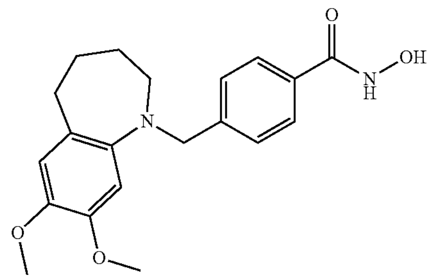
T-10
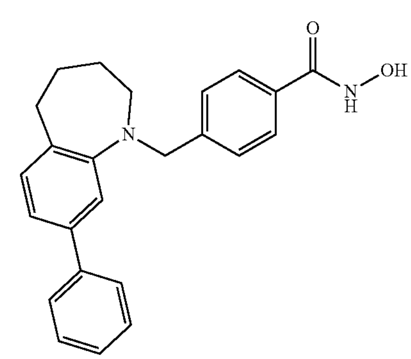
T-11
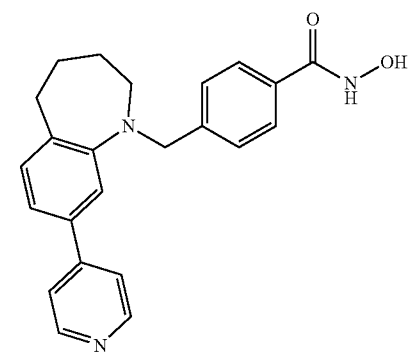
T-12
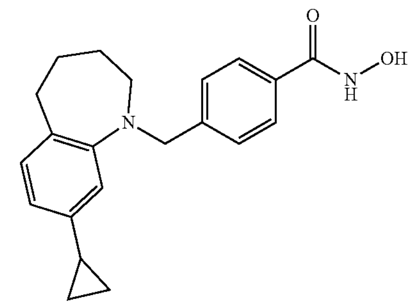
T-13
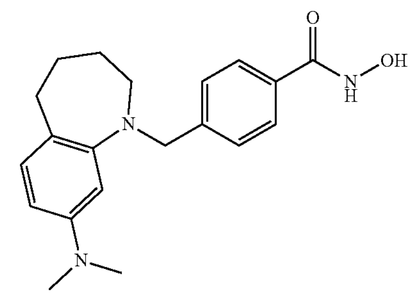

-continued
T-14
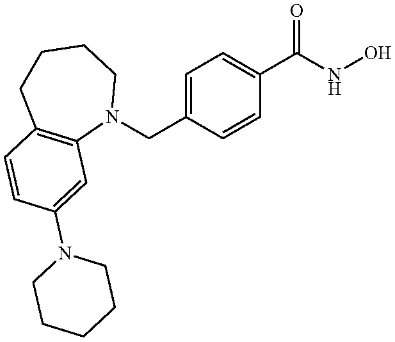
T-15
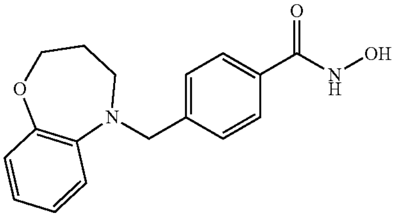
T-16
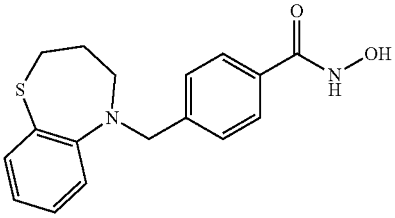
T-17
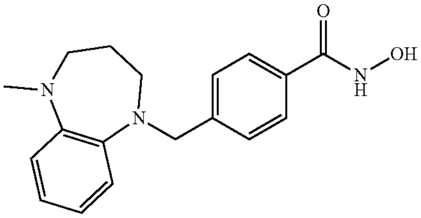
T-18
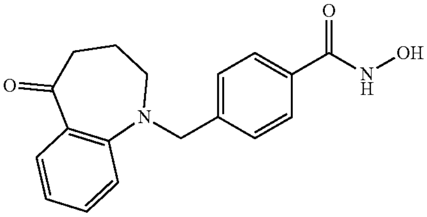
T-19
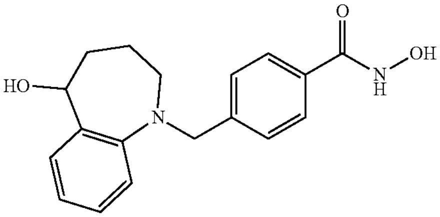
-continued
T-20
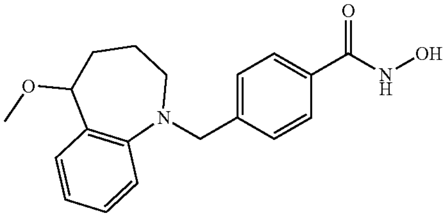
T-21
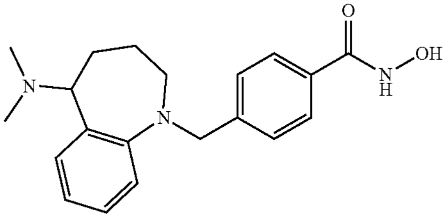
T-22
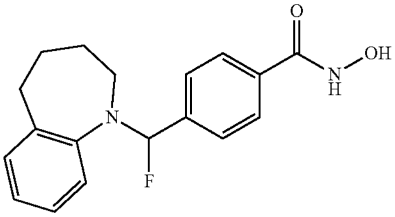
T-23
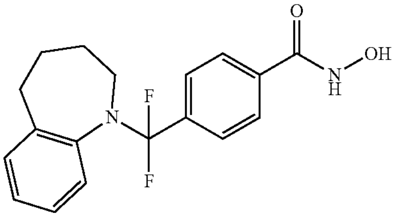
T-24
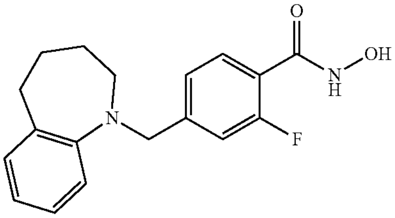
T-25
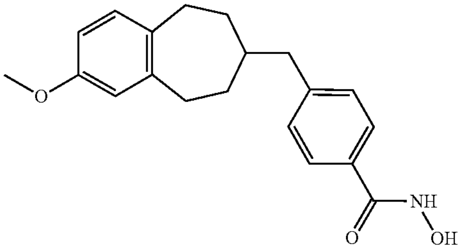

-continued

T-26

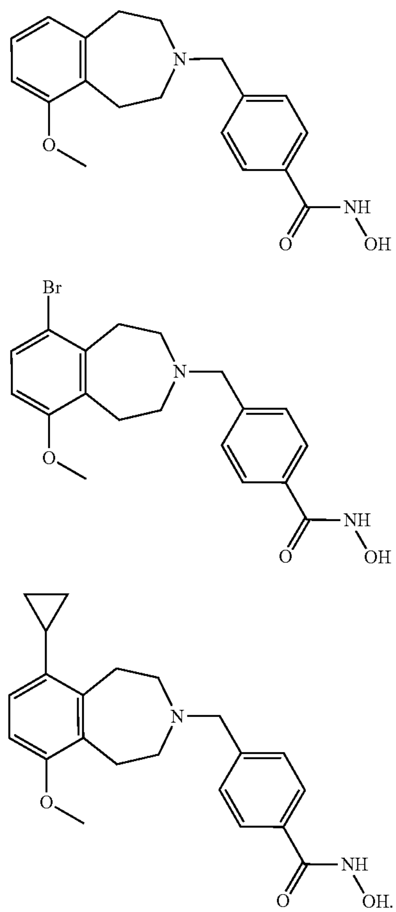

T-27

T-28

In the present disclosure, the benzonitric heterocyclic compound represented by formula I or the pharmaceutically acceptable salt thereof has one or more chiral carbon atoms, so the compound can be separated to obtain optical purity isomers, for example pure enantiomers, racemates or mixed isomers. Pure single isomers can be obtained by separation methods in the art, for example obtained by chiral crystallization into salt, or separation of chiral preparative column.

In the present disclosure, the benzonitric heterocyclic compound represented by formula I or the pharmaceutically acceptable salt thereof can exist a crystal form or an amorphous form. The term "crystal form" means that the ions or molecules are arranged in a strictly periodic manner in three-dimensional space in a certain manner, and have the regularity of periodic repetition at a certain distance; due to the difference in the above-mentioned periodic arrangement, there can be multiple crystal forms, that is, polymorphism. The term "amorphous" means that the ions or molecules are in a disordered distribution state, that is, there is no periodic arrangement between ions and molecules.

In the present disclosure, if the benzonitric heterocyclic compound represented by formula I or the pharmaceutically acceptable salt thereof exists a stereoisomer, the benzonitric heterocyclic compound can exist as a single stereoisomer or a mixture thereof (for example, racemate). The term "stereoisomer" refers to cis-trans isomer or optical isomer. These stereoisomers can be separated, purified and enriched by asymmetric synthesis methods or chiral separation methods (including but are not limited to thin layer chromatography, rotary chromatography, column chromatography, gas chromatography, high pressure liquid chromatography, etc.), and can also be obtained by chiral resolution by bonding (chemical bonding, etc.) or salifying (physical bonding, etc.), etc. with other chiral compounds. The term "single stereoisomer" means that the mass content of one stereoisomer of the compound of the present disclosure relative to all stereoisomers of the compound is not less than 95%.

In the present disclosure, if the benzonitric heterocyclic compound represented by formula I or the pharmaceutically acceptable salt thereof exists a tautomer, the benzonitric heterocyclic compound can exist as a single tautomer or a mixture thereof, preferably in the form of a relatively stable tautomer.

The present disclosure also includes isotopically-labeled benzonitric heterocyclic compounds represented by formula I or the pharmaceutically acceptable salt thereof of the present disclosure, wherein one or more atoms are substituted by one or more atoms having a specific atomic mass or mass number. Examples of isotopes that can be incorporated into the compounds of the present disclosure include but are not limited to the isotopes of hydrogen, carbon, nitrogen, oxygen, fluorine, sulfur and chlorine (e.g., $^{2}H$, $^{3}H$, $^{13}C$, $^{14}C$, $^{15}N$, $^{18}O$, $^{17}O$, $^{18}F$, $^{35}S$ and $^{36}Cl$). Isotopically labeled compounds of the present disclosure can be used to determine the tissue distribution of compounds, prodrugs thereof and metabolites thereof; preferably isotopes for such assays include $^{3}H$ and $^{14}C$. Furthermore, in some cases, substitution with heavier isotopes (e.g., deuterium (2H or D)) can provide increased metabolic stability, which provides therapeutic advantages, such as increased in vivo half-life or reduced dose requirements.

Isotopically-labeled compounds of the present disclosure can generally be prepared according to the methods described herein by replacing non-isotopically labeled reagents with isotopically labeled reagents.

In the present disclosure, the benzonitric heterocyclic compound represented by formula I or the pharmaceutically acceptable salt can be synthesized by methods similar to that known in the chemical field, and the steps and conditions can refer to similar reactions in the art, in particular according to the disclosure herein. Starting materials are typically from commercial sources such as Aldrich or can be easily prepared using the method well known to those skilled in the art (obtained through SciFinder, Reaxys online database).

In the present disclosure, the benzonitric heterocyclic compound represented by formula I or the pharmaceutically acceptable salt thereof can also be prepared by the prepared benzonitric heterocyclic compound represented by formula I or the pharmaceutically acceptable salts thereof, using the conventional method in the art, through peripheral modification to obtain other benzonitric heterocyclic compound represented by formula I or the pharmaceutically acceptable salt thereof.

The necessary raw materials or reagents for the preparation of benzonitric heterocyclic compound represented by formula I or pharmaceutically acceptable salt thereof can be obtained commercially, or prepared by synthetic methods known in the art. The method described in the following experimental section can be used to prepare the compound of the present disclosure of free alkali or salt formed by adding acid. The term pharmaceutically acceptable salt refers to the pharmaceutically acceptable salt as defined herein, and has all the effects of the parent compound. Pharmaceutically acceptable salts can be prepared by adding the corresponding acid into a suitable organic solvent of an organic base, and treating according to a conventional method.

Examples of salt formation include: for base addition salts, it is possible by using alkali metal or alkaline earth metal hydroxides or alkoxides (such as ethoxide or methoxide) or suitable basic organic amines (such as diethanolamine, choline, meglumine) to treat the compounds of the present disclosure with suitable acidic protons for the preparation of alkali metal (such as sodium, potassium or lithium) or alkali-earth metal (such as aluminum, magnesium, calcium, zinc or bismuth) salts.

Or, for acid addition salts, salts formed with inorganic acids, for example hydrochloric acid, hydrobromic acid, sulfuric acid, nitric acid, phosphoric acid; and salts formed with organic acids, for example acetic acid, benzenesulfonic acid, benzoic acid, camphorsulfonic acid, citric acid, ethanesulfonic acid, fumaric acid, glucoheptonic acid, glutamic acid, glycolic acid, hydroxynaphthoic acid, 2-hydroxyethanesulfonic acid, lactic acid, maleic acid, malic acid, oxalic acid, pyruvic acid, malonate acid, mandelic acid, methanesulfonic acid, mucofuroic acid, 2-naphthalenesulfonic acid, propionic acid, salicylic acid, succinic acid, tartaric acid, citric acid, cinnamic acid, p-toluenesulfonic acid or trimethylacetic acid.

The term "compound of the present disclosure" or "compound represented by the present disclosure" includes any benzonitric heterocyclic compounds represented by formula I or pharmaceutically acceptable salts thereof. The compounds of the present disclosure can also exist in the form of hydrates or solvates.

The present disclosure also provides a preparation method of the above-mentioned benzonitric heterocyclic compound represented by formula I, comprising the following steps: in a solvent, performing a hydroxylamine reaction as shown below between a compound represented by formula II with hydroxylamine to obtain the benzonitric heterocyclic compound represented by formula I;

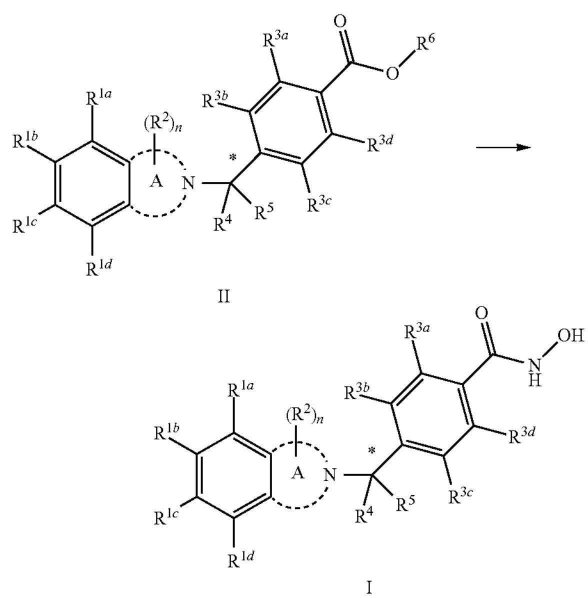

II

I wherein, *, ring A, n, $R^2$, $R^{1a}$, $R^{1b}$, $R^{1c}$, $R^{1d}$, $R^{3a}$, $R^{3b}$, $R^{3c}$, $R^{3d}$, $R^4$ and $R^5$ are as defined above; $R^6$ is $C_1$-$C_6$ alkyl (for example, $C_1$-$C_4$ alkyl: methyl, ethyl, n-propyl, isopropyl, n-butyl, isobutyl, sec-butyl or tert-butyl; for another example, methyl or ethyl).

In preparation method of the benzonitric heterocyclic compound represented by formula I, the conditions and operations of the hydroxylamine reaction can be the conventional conditions and operations in such reactions in the art; in the present disclosure, the following are preferred:

wherein, the solvent can be an alcohol solvent, for example, methanol and/or ethanol.

The amount of the solvent can be used without affecting the reaction, for example, the mass-volume ratio of the compound represented by formula II to the solvent is 0.1 g/L to 20 g/L (for example, 5 g/L to 15 g/L).

The molar ratio of the compound represented by formula II to the hydroxylamine can be 1:5 to 1:50 (for example, 1:40 to 1:48).

The temperature of the hydroxylamine reaction can be room temperature to 80° C. (for example, 10 to 30° C.).

The process of the hydroxylamine reaction can be monitored using conventional monitoring methods in the art (for example, TLC, HPLC, or NMR), and the reaction endpoint is generally taken when the compound represented by formula II disappears or no longer reacts.

The preparation method can also comprise a post-treatment; the post-treatment can comprise the following steps: after the hydroxylamine reaction is finished, adjusting the pH to neutral, concentrating, adding with the organic solvent, washing with water (removing the hydroxylamine), drying the organic phase, concentrating, separating and purifying; and adjusting the pH to neutral using a conventional acid, for example 1N hydrochloric acid; the organic solvent can be ester solvent, for example ethyl acetate. The separation and purification are preferably column chromatography separation or crystallization; the solvent of the crystallization can be a mixed solvent of alcohol solvent (for example, ethanol) and water.

The preparation method further comprises the following steps: in a solvent, under the exist of a base, performing a coupling reaction as shown below between a compound represented by formula III with a compound represented by formula IV to obtain the compound represented by formula II;

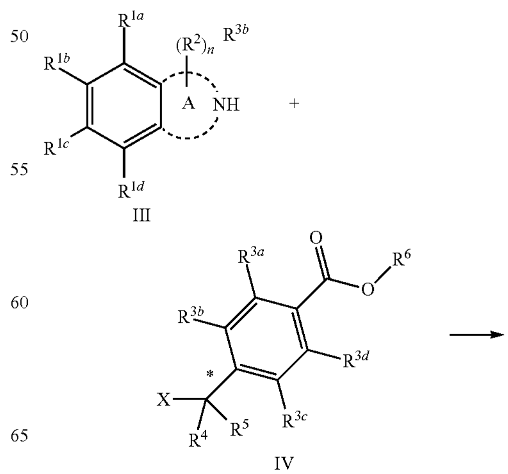

III

IV

-continued

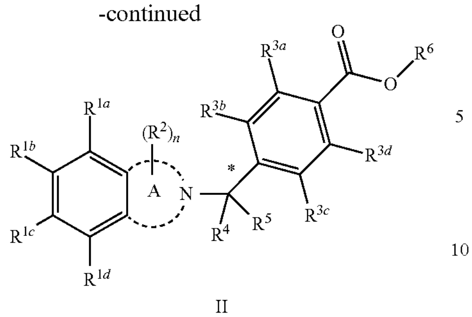

II wherein, $R^6$, *, ring A, n, $R^2$, $R^{1a}$, $R^{1b}$, $R^{1c}$, $R^{1d}$, $R^{3a}$, $R^{3b}$, $R^{3c}$, $R^{3d}$, $R^4$ and $R^5$ are as defined above; X is halogen (for example, bromine or chlorine).

In preparation method of the benzonitric heterocyclic compound represented by formula I, the conditions and operations of the coupling reaction can be the conventional conditions and operations in such reactions in the art; in the present disclosure, the following are preferred:

wherein, the solvent can be an amide solvent, for example, N,N-dimethylformamide (DMF).

The amount of the solvent can be used without affecting the reaction, for example, the mass-volume ratio of the compound represented by formula II to the solvent is 1 g/L to 50 g/L (for example, 35 g/L to 45 g/L).

The molar ratio of the compound represented by formula III to the compound represented by formula IV can be 0.8:1 to 1:0.8 (for example, 1:1).

The base can be inorganic base and/or organic base, and the inorganic base can be alkali metal carbonate, for example, one or more of sodium carbonate, potassium carbonate and lithium carbonate.

The molar ratio of the base to the compound represented by formula IV can be 0.8:1 to 3:1 (for example, 1:1 to 2:1, for another example, 1.5:1).

The temperature of the coupling reaction can be room temperature to 150° C. (for example, 80 to 120° C., for another example, 100° C.).

The process of the coupling reaction can be monitored using conventional monitoring methods in the art (for example, TLC, HPLC, or NMR), and the reaction endpoint is generally taken when the compound represented by formula III disappears or no longer reacts.

The preparation method can also comprise a post-treatment; the post-treatment can comprise the following steps: after the coupling reaction is finished, adding with water, extracting the organic solvent. drying the organic phase, concentrating, separating and purifying; and the organic solvent can be ester solvent, for example, ethyl acetate. The separation and purification are preferably column chromatography separation or crystallization; the filler of the column chromatography can be silica gel filler.

The present disclosure also provides a compound represented by formula II,

II

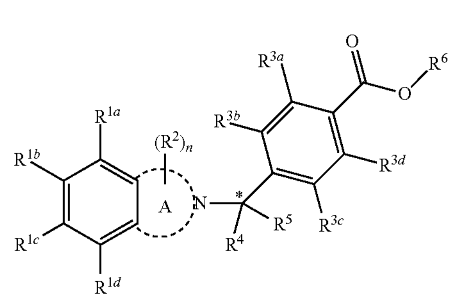

wherein, $R^6$, *, ring A, n, $R^2$, $R^{1a}$, $R^{1b}$, $R^{1c}$, $R^{1d}$, $R^{3a}$, $R^{3b}$, $R^{3c}$, $R^{3d}$, $R^4$ and $R^5$ are as defined above.

In a certain embodiment, the compound represented by formula II can be any one of the following structures:

1-8

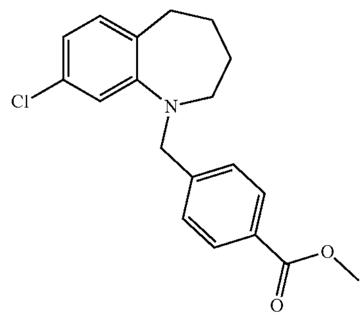

3-4

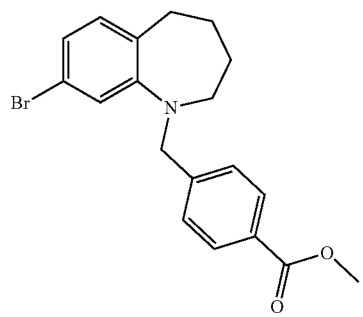

23-6

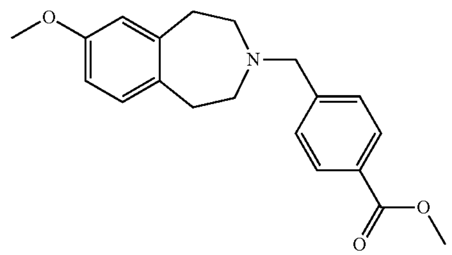

The present disclosure provides a pharmaceutical composition, comprising the above-mentioned benzonitric heterocyclic compound represented by formula I or the pharmaceutically acceptable salt thereof, and one or more pharmaceutically acceptable carriers. In the pharmaceutical composition, the amount of the benzonitric heterocyclic compound represented by formula I or the pharmaceutically acceptable salt thereof can be a therapeutically effective amount.

The pharmaceutically acceptable carriers (pharmaceutical excipients) can be those excipients widely used in the art of pharmaceutical production. Excipients are mainly used to provide a safe, stable and functional pharmaceutical composition, and can also provide a method for allowing a subject to receive the administration of an active ingredient to dissolve at a desired rate, or facilitating effective absorption of the active ingredient after the subject receives the administration of the composition. The pharmaceutical excipients can be inert fillers or provide certain functions, for example stabilizing the overall pH value of the composition or preventing the degradation of active ingredients of the composition. The pharmaceutical adjuvants can include one or more of the following adjuvants: binders, suspending agents, emulsifiers, diluents, fillers, granulating agents, adhesives, disintegrating agents, lubricants, anti-sticking agents, glidants, wetting agents, gelling agents, absorption delaying agents, dissolution inhibitors, enhancers, adsorbents, buffers, chelating agents, preservatives, colorants, flavors and sweeteners.

The pharmaceutical composition of the present disclosure can be prepared by any method known to those skilled in the art according to the disclosure. For example, conventional mixing, dissolving, granulating, emulsifying, levigating, encapsulating, entrapping or lyophilizing processes.

The pharmaceutical composition of the present disclosure can be administered in any form, including injection (intravenous), mucosal, oral (solid and liquid preparations), inhalation, ocular, rectal, topical or parenteral (infusion, injection, implantation, subcutaneous, intravenous, intra-arterial and intramuscular) administration. The pharmaceutical composition of the present disclosure can also be a controlled release or delayed release dosage form (for example, liposome or microsphere). Examples of solid oral formulations include, but are not limited to, powders, capsules, caplets, soft capsules, and tablets. Examples of liquid formulations for oral or mucosal administration include, but are not limited to, suspensions, emulsions, elixirs, and solutions. Examples of topical preparations include, but are not limited to, emulsions, gels, ointments, creams, patches, pastes, foams, lotions, drops or serum formulations. Examples of parenteral preparations include, but are not limited to, injection solutions, dry preparations that can be dissolved or suspended in pharmaceutically acceptable carriers, injection suspensions and injection emulsions. Examples of other suitable preparations of the pharmaceutical composition include, but are not limited to, eye drops and other ophthalmic preparations; aerosols: such as nasal sprays or inhalants; liquid dosage forms suitable for parenteral administration; suppositories and lozenges.

The present disclosure also provides a use of the above-mentioned benzonitric heterocyclic compound represented by formula I or the pharmaceutically acceptable salt thereof or the above-mentioned pharmaceutical composition in the manufacture of a HDAC inhibitor. The HDAC is preferably HDAC6.

In the use, the HDAC inhibitor can be used in mammalian organisms; can also be used in vitro, mainly for experimental purposes, for example, providing comparison as a standard sample or a control sample, or preparing a kit according to the conventional method in the art, so as to provide a rapid detection for the inhibition effect of HDAC6.

The present disclosure also provides a use of the benzonitric heterocyclic compound represented by formula I or the pharmaceutically acceptable salt thereof or the above-mentioned pharmaceutical composition in the manufacture of a medicament. The medicament can be used for preventing and/or treating cancer, nervous diseases or autoimmune diseases; or, the medicament can be a medicament for preventing and/or treating diseases or disorders related to HDAC.

The present disclosure also provides a use of the benzonitric heterocyclic compound represented by formula I or the pharmaceutically acceptable salt thereof or the above-mentioned pharmaceutical composition in the manufacture of a medicament for preventing and/or treating diseases or disorders related to HDAC; the HDAC is preferably HDAC6; the diseases or disorders related to HDAC can be cancer, nervous diseases or autoimmune diseases; the medicament can achieve the effect of preventing and/or treating cancer, nervous diseases or autoimmune diseases by regulating HDAC expression and/or activity.

The present disclosure also provides a method for preventing and/or treating cancer, nervous diseases or autoimmune diseases (such as HDAC-related, the HDAC is preferably HDAC6), comprising administering a therapeutically effective amount of the benzonitric heterocyclic compound represented by formula I or the pharmaceutically acceptable salt thereof or the above-mentioned pharmaceutical composition to a subject in need thereof, such as a human.

The present disclosure also provides a method for inhibiting cell proliferation or cancer in vitro or in vivo, comprising contacting cells with an effective amount of the benzonitric heterocyclic compound represented by formula I or the pharmaceutically acceptable salt thereof or the above-mentioned pharmaceutical composition.

The above-mentioned cancers can be ovarian cancer, colon cancer, breast cancer, liver cancer, pancreatic cancer, gallbladder cancer, gastrointestinal cancer, head and neck cancer, cervical cancer, prostate cancer, lung cancer, melanoma, germ cell tumor, gestational trophoblastic tumors, glioblastoma, myeloma, neuroblastoma-derived CNS tumors, monocytic leukemia, B-cell-derived leukemia, T-cell-derived leukemia, B-cell-derived lymphoma, T-cell-derived lymphoma and mast cell-derived tumors, and the combination thereof.

The above-mentioned nervous diseases can be neurodegenerative diseases (such as Alzheimer's disease, Parkinson's disease, Huntington's chorea, amyotrophic lateral sclerosis, spinocerebellar degeneration, Rett's syndrome), peripheral neuropathy (such as peroneal muscular atrophy, giant axonal neuropathy (GAN)), and the combination thereof.

The above-mentioned autoimmune diseases can be psoriasis, inflammatory diseases (for example, osteoarthritis, rheumatoid arthritis, colitis), and diseases that can be treated by immunomodulation (for example, multiple sclerosis, autoimmune diabetes, lupus, atopic dermatitis, allergy, asthma, allergic rhinitis, inflammatory bowel disease).

When used as a medicament, the benzonitric heterocyclic compound represented by formula I or the pharmaceutically acceptable salt thereof can be administered in the form of pharmaceutical composition. The composition can be prepared according to methods well known in the pharmaceutical field, and can be administered in various ways, depending on the need for topical or systemic treatment and the area to be treated. Administration can be topical (including epidermal and transdermal, ocular and mucosal delivery, including intranasal, vaginal and rectal delivery), pulmonary (for example, inhalation or insufflation through powder or aerosol, including nebulizer; intratracheal or intranasal), oral or parenteral administration. Oral administration can include dosage forms formulated for once-daily or twice-daily (BID) administration. Parenteral administration includes intravenous, intraarterial, subcutaneous, intraperitoneal intramuscular injection or infusion; or intracranial, for example intrathecal or intraventricular. Parenteral administration can be in the form of a single bolus dose, or can be through a continuous infusion pump. Pharmaceutical compositions and formulations for topical administration can include transdermal patches, ointments, emulsions, ointments, gels, drops, suppositories, sprays, liquids and powders. Conventional pharmaceutical carriers, water, powder or oily substrates, thickeners, etc. may be necessary or required.

As used herein, the term "treatment" refers to therapeutic or palliative measures. Beneficial or desired clinical outcomes include, but are not limited to: total or partial alleviation of the disease or disorder or condition related symptoms, reduction of disease severity, stabilization (i.e., not worsening) of the disease condition, delaying or slowing the progression of the disease, relieving or mitigating of the disease status (for example, one or more symptoms of the disease), and detectable or undetectable remission (whether partial or total). "Treatment" can also refer to prolonging the survival time compared with the expected survival time without treatment.

In certain embodiments, the benzonitric heterocyclic compound represented by formula I or the pharmaceutically acceptable salt thereof or the above-mentioned pharmaceutical composition can be used to prevent diseases and conditions as defined herein (for example, autoimmune disease, neurological disease, and cancer). The term "prevent" as used herein means to prevent, in whole or in part, the onset, recurrence or spread of a disease or condition or symptoms thereof described herein.

The term "pharmaceutical excipient" or "excipient" refers to a pharmaceutically acceptable chemical substance, for example, an agent known to those of ordinary skill in the art of pharmacy to aid in the administration of pharmaceuticals. It is a compound that can be used to prepare a pharmaceutical composition that is generally safe, non-toxic, and biologically or otherwise undesirable, including excipients that are pharmaceutically acceptable for veterinary and human administration. Common excipients include binders, surfactants, diluents, disintegrants and lubricants.

Unless otherwise stated, the following definitions as used herein should be applied. For the purposes of the present disclosure, chemical elements are in accordance with the Chemical Elements and Periodic Table of Elements, CAS Edition, and "Handbook of Chemistry and Physics", 75th Edition, 1994. In addition, general principles of organic chemistry can be referred to the description of "Organic Chemistry", Thomas Sorrell, University Science Books, Sausalito: 1999, and "March's Advanced Organic Chemistry" by Michael B. Smith and Jerry March, John Wiley & Sons, New York: 2007, the entire contents of which are incorporated herein by reference.

In this specification, groups and their substituents can be selected by those skilled in the art to provide stable structural moieties and compounds. When a substituent is described by a conventional chemical formula written from left to right, the substituent also includes the chemically equivalent substituent obtained when the structural formula is written from right to left.

Certain chemical groups defined herein are preceded by abbreviated symbols to indicate the total number of carbon atoms present in the group. For example, $C_1$-$C_6$ alkyl refers to an alkyl group as defined below having a total of 1, 2, 3, 4, 5 or 6 carbon atoms. The total number of carbon atoms in the abbreviated symbol does not include the carbon that may be present in the substituent of the group.

In the present disclosure, numerical ranges defined in substituents, for example 0 to 4, 1 to 4, 1 to 3, etc., indicate integers in the ranges, for example, 1 to 6 is 1, 2, 3, 4, 5, 6.

In addition to the foregoing, when used in the specification and claims of the present disclosure, the following terms have the meanings shown below unless specifically indicated otherwise.

The term "one or more" or "one or two or more" means 1, 2, 3, 4, 5, 6, 7, 8, 9 or more.

The term "comprising" is an open definition that includes the contents specified in the present disclosure, but does not exclude other aspects.

The term "substituted" means one or more than one hydrogen atom(s) on a specific atom are substituted with the substituent, including deuterium and hydrogen variables, as long as the valence of the specific atom is normal and the substituted compound is stable.

In general, the term "substituted" means that one or more hydrogen atoms in a given structure have been substituted with a specified substituent. Further, when the group is substituted by one or more of the substituents, the substituents are independent of each other, that is, the one or more substituents may be different from each other or the same. Unless otherwise indicated, a substituent group can be substituted at each substitutable position of the substituted group. When more than one position in the given structural formula can be substituted by one or more substituents selected from specific groups, the substituents can be substituted at each position in the same or different way.

In various parts of the specification, the substituents of the compounds disclosed in the present disclosure are disclosed in terms of group type or scope. In particular, the present disclosure includes each independent secondary combination of each member of the kind and range of these group. The term "$C_x$-$C_y$ alkyl" refers to a linear or branched saturated hydrocarbons containing x to y carbon atoms. For example, the term "$C_1$-$C_6$ alkyl" or "$C_{1-6}$ alkyl" specifically refers to independently disclosed methyl, ethyl, $C_3$ alkyl, $C_4$ alkyl, $C_5$ alkyl and $C_6$ alkyl; "$C_{1-4}$ alkyl" refers to independently disclosed methyl, ethyl, $C_3$ alkyl (i.e., propyl, including n-propyl and isopropyl), $C_4$ alkyl (i.e., butyl, including n-butyl, isobutyl, sec-butyl and tert-butyl).

The term "halogen" is selected from F, Cl, Br or I, especially F or Cl.

The term "alkoxy" refers to the group —O—$R^X$, wherein $R^X$ is an alkyl as defined above.

In the present disclosure, the term "alkyl" as part of a group or other group (for example, in a group such as an alkyl substituted by halogen, etc.) means that it includes branched and linear chain saturated aliphatic hydrocarbon with a specified number of carbon atoms; for example, a linear or branched saturated hydrocarbon chain containing 1 to 20 carbon atoms; for another example, $C_1$-$C_6$ alkyl. As defined in "$C_1$-$C_6$ alkyl", it includes groups having 1, 2, 3, 4, 5, or 6 carbon atoms in a linear or branched chain structure. Where propyl is $C_3$ alkyl (including isomers, for example, n-propyl or isopropyl); butyl is $C_4$ alkyl (including isomers, for example, n-butyl, sec-butyl, isobutyl or tert-butyl); pentyl is $C_5$ alkyl (including isomers, for example, n-pentyl, 1-methyl-butyl, 1-ethyl-propyl, 2-methyl-1-butyl, 3-methyl-1-butyl, isopentyl, tert-pentyl or neopentyl); hexyl is $C_6$ alkyl (including isomers, for example, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl). In addition, heptyl is $C_7$ alkyl (including isomers, for example, n-heptyl, 2,4-dimethylpentyl, 2,2-dimethylpentyl, 3,3-dimethylpentyl, 2-ethylpentyl and 3-ethylpentyl). Octyl is $C_8$ alkyl (including isomers, for example, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl). Nonyl is $C_9$ alkyl (including isomers, for example, n-nonyl, 2-methyl-2-ethylhexyl, 2-methyl-3-ethylhexyl, 2,2-diethylpentyl). Decyl is $C_{10}$ alkyl (including isomers, for example, n-decyl, 3,3-diethylhexyl, 2,2-diethylhexyl). In a certain embodiment, the "alkyl" is preferably a linear or branched chain alkyl containing 1 to 6 carbon atoms. In a certain embodiment, the "alkyl" refers to $C_1$-$C_6$ alkyl. In a certain embodiment, the "alkyl" refers to $C_1$-$C_4$ alkyl.

The terms "moiety", "structural moiety", "chemical moiety", "group", "chemical group" as used herein refer to a specific fragment or functional group in a molecule. Chemical moieties are usually considered as chemical entities embedded or attached to molecules.

When the listed substituent does not indicate through which atom it is attached to a compound included in the general formula but not specifically mentioned, such substituent may be bonded through any of its atoms. A combination of the substituent and/or the variant thereof is allowed only when the combination results in a stable compound.

When the listed groups do not explicitly indicate that they have substituents, such groups only refer to unsubstituted ones. For example, when "$C_1$-$C_4$ alkyl" is not limited by "substituted or unsubstituted", it only refers to "$C_1$-$C_4$ alkyl" itself or "unsubstituted $C_1$-$C_4$ alkyl".

In various parts of the present disclosure, linking substituents are described. When the structure clearly requires a linking group, the Markush variables listed for that group should be understood to be the linking group. For example, if the structure requires a linking group and "alkyl" is listed for the definition of Markush group of this variable, it should be understood that the "alkyl" represents the linked alkylene group.

In some specific structures, when the alkyl is clearly represented as a linking group, the alkyl represents the linked alkylene, for example, $C_1$-$C_6$ alkyl in the group "halo-$C_1$-$C_6$ alkyl" should be understood as $C_1$-$C_6$ alkylene.

The term "alkylene" refers to a saturated divalent hydrocarbyl group obtained by removing two hydrogen atoms from a saturated linear or branched chain hydrocarbyl group. Examples of alkylene groups include methylene ($-CH_2-$), ethylene {including $-CH_2CH_2-$ or $-CH(CH_3)-$}, isopropylidene {including $-CH(CH_3)CH_2-$ or $-C(CH_3)_2-$}, etc.

The term "cycloalkyl" refers to a saturated monocyclic or polycyclic carbocyclic substituent consisting only of carbon and hydrogen atoms and which can be attached to the rest of the molecule by a single bond through any suitable carbon atom; when it is a polycyclic, it can be a fused-linked, bridged-linked, or spiro-linked (i.e., two gem hydrogens on a carbon atom are substituted by an alkylene) fused ring system, bridged ring system, or spiro ring system. In a certain embodiment, typical monocyclic cycloalkyl groups is for example, cyclopropyl, cyclobutyl, cyclopentyl, cyclohexyl or cycloheptyl.

The term "heterocycloalkyl" refers to a saturated cyclic group with heteroatoms, containing one or more heteroatoms independently selected from N, O, S, S(=O) and $S(=O)_2$ with the rest being carbon, forming a stable 3- to 10-membered saturated heterocyclic system. Unless otherwise specified in the specification, the heterocycloalkyl group may be monocyclic ("monocyclic heterocycloalkyl") or a bicyclic, tricyclic or polycyclic ring system, which may include a fused, bridged or spiro ring system (for example, bicyclic system ("bicyclic heterocycloalkyl")). The ring system of a bicyclic heterocycloalkyl can include one or more heteroatoms in one or both rings; and is saturated. Exemplary 3-membered heterocyclyl groups include, but are not limited to, aziridinyl, oxiranyl, and thiacyclopropyl, or stereoisomers thereof; exemplary 4-membered heterocyclyl groups including, but are not limited to, azetidinyl, epoxypropyl, thiacyclobutyl, or isomers and stereoisomers thereof, exemplary 5-membered heterocyclyl groups include, but are not limited to, tetrahydrofuryl, tetrahydrothienyl, pyrrolidinyl, thiazolidinyl, isothiazolidinyl, oxazolidinyl, isoxazolidinyl, imidazolidinyl, pyrazolidinyl, dioxolanyl, oxathiofuryl, dithiofuryl, or isomers and stereoisomers thereof. Exemplary 6-membered heterocyclyl groups include, but are not limited to, piperidinyl, tetrahydropyranyl, thiocyclopentyl, morpholinyl, thiomorpholinyl, dithianyl, dioxanyl, piperazinyl, triazinyl, or isomers and stereoisomers thereof, exemplary 7-membered heterocyclyl groups include, but are not limited to, azepanyl, oxacycloheptyl, thiocycloheptyl, and diazecycloheptyl, or isomers and stereoisomers thereof. And in a certain embodiment, tetrahydroquinolyl, tetrahydrotriazolopyrazinyl or diazepanyl. In one embodiment, a typical 5- to 6-membered monocyclic heterocyclyl containing one or more heteroatoms independently selected from N, O, and S. In one embodiment, "heterocycloalkyl" is a 4- to 6-membered heterocycloalkyl, wherein the heteroatom is selected from one or more of N, O and S, and the number of heteroatoms is 1, 2 or 3.

The term "aryl" refers to an all-carbon aromatic group with a fully conjugated π electron system, which can be a monocyclic or fused ring, and usually has 6-14 carbon atoms, preferably 6-12 carbon atoms, and most preferably 6 carbon atoms. Examples of aryl include, but are not limited to, phenyl, naphthyl and anthracyl.

The term "heteroaryl" refers to an aromatic group containing heteroatoms, which can be monocyclic or fused ring, preferably 5- to 12-membered heteroaryl containing 1 to 4 heteroatoms independently selected from N, O and S, including but are not limited to pyrrolyl, furyl, thienyl, indolyl, imidazolyl, oxazolyl, isoxazolyl, pyrazolyl, pyridyl, pyrimidinyl, pyrazinyl, pyridazinyl, quinolyl, isoquinolinyl, (benzo)oxazolyl, (benzo)furyl, (benzo)thienyl, (benzo)thiazolyl, triazolyl. In a certain embodiment, a typical 5- to 6-membered monocyclic heteroaryl contains one or more heteroatoms independently selected from N, O, and S. In a certain embodiment, "heteroaryl" is a 5- to 6-membered heteroaryl, wherein the heteroatom is selected from one or more of N, O and S, and the number of heteroatoms is 1, 2 or 3.

Unless otherwise specified, all technical terms and scientific terms used herein have standard meanings in the art to which the claimed subject matter belongs. If more than one definition exists for a term, the definitions herein prevail.

It should be understood that singular forms such as "a" used in the present disclosure include plural referents unless otherwise specified. In addition, the term "comprise" is an open definition rather than a closed one, that is, it includes the contents specified in the present disclosure, but does not exclude other aspects.

Unless otherwise specified, the present disclosure adopts the conventional methods of mass spectrometry and elemental analysis, and the steps and conditions can be referred to the conventional operating steps and conditions in the art.

Unless otherwise specified, the present disclosure adopts standard nomenclature and standard laboratory procedures and techniques of analytical chemistry, organic synthetic chemistry and optics. In some cases, standard techniques are used in chemical synthesis, chemical analysis, and performance testing of light emitting devices.

Furthermore, it should be noted that, unless otherwise explicitly specified, the description mode " . . . be independently" used in the present disclosure should be understood in a broad sense, which means that the described individuals are independent of each other and can be the same or different specific groups independently. More specifically, the description mode " . . . be independently" can mean that the specific options expressed by the same symbols in different groups do not affect each other; it can also mean that in the same group, the specific options expressed by the same symbols do not affect each other.

Those skilled in the art can understand that, according to the conventions used in the art, the

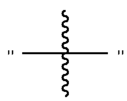

used in the structural formula of a group described in the present disclosure means that the corresponding group is connected with other fragments and groups in the compound through this site.

On the basis of not violating the common sense in the art, the above-mentioned preferred conditions can be arbitrarily combined to obtain the preferred examples of the present disclosure.

The reagents and raw materials used in the present disclosure are commercially available.

The positive progressive effect of the present disclosure is that pharmacological experiments show that the benzonitric heterocyclic compounds of the present disclosure have the following beneficial effects:

1) The compounds of the present disclosure have higher inhibitory activity on HDAC6 (nearly half of the compounds have $IC_{50}$<10 nM for HDAC6 inhibitory activity), and show better selective inhibitory activity (the inhibitory activity $IC_{50}$ against HDAC1 are all >250 nM; the selectivity for HDAC1/HDAC6 is mostly more than 30 times in most cases, and more than 50 times in some cases), the selectivity of the compound of the present disclosure is better than that of Rocilinostat (ACY-1215), a clinical I/II drug of HDAC6 inhibitor, and better than that of SW-100.
2) The compounds of the present disclosure have a weak inhibitory effect on normal cells while effectively inhibiting multiple tumor cells, and exhibit good cell selective inhibitory activity.
3) The compounds of the present disclosure show a dose-dependent protective effect on HCA-induced neuron cell oxidative stress in a cell model, suggesting that it has a certain neuroprotective effect.
4) The compounds of the present disclosure have weak inhibitory activity on hERG and less potential cardiotoxicity; single oral gavage in rats has high tolerance and low acute toxicity.
5) In particular, the in vivo drug metabolism test shows that the compound of the present disclosure has ideal pharmacokinetic characteristics, has higher blood-brain barrier permeability, and has better brain permeability than the six-membered ring positive control compound SW-100 and the five-membered ring positive control compound II-ING-39.

To sum up, the advantages of the benzonitric heterocyclic compounds of the present disclosure are that the compounds have selective and high inhibitory activity on HDAC6, the potential risk of affecting the heart is small, the animal tolerance is high, and the compounds show better anti-proliferation activity on multiple tumor cells in vitro and the compounds have weak toxicity on normal human cells, and are expected to be used as a targeted anti-tumor drug with high efficiency and low toxicity. At the same time, the benzonitric heterocyclic compound of the present disclosure has a protective effect on neurocytes in vitro, pharmacokinetics in vivo shows high blood-brain barrier properties, and can also be used as a drug for the treatment of neurodegenerative diseases.

The compounds of the present disclosure have novel structures, and the efficacy and safety of the compounds reflect better inventiveness. The present disclosure has prominent novelty and notable scientific progress.

BRIEF DESCRIPTION OF THE DRAWINGS

FIG. 1 is the cell survival rate in the HCA-induced neuronal toxicity model

DETAILED DESCRIPTION OF THE PREFERRED EMBODIMENT

The present disclosure is further described below by way of embodiments, but the present disclosure is not thereby limited to the scope of the described embodiments. The experimental methods not specified in the specific conditions in the following embodiments are selected according to the conventional methods and conditions, or according to the commodity instructions.

In the following embodiments, the abbreviations are explained:

DCM: dichloromethane; PE: petroleum ether; EA: ethyl acetate; DMF: N,N-dimethylformamide; THF: tetrahydrofuran; MeOH: methanol; p-TsCl: p-toluenesulfonyl chloride; t-BuOK: potassium tert-butoxide; pyridine: pyridine; toluene: toluene; concd: concentrated; PPA: polyphosphoric acid; DIBALH: diisobutylaluminum hydride.

In the following embodiments, room temperature refers to 10 to 30° C.; overnight refers to 8 to 15 hours, for example, 12 hours; eq refers to equivalent; and solvent ratios (for example, PE/EA) refer to volume ratios.

The compounds of the present disclosure can be prepared by the following synthetic general method:

General Method I:

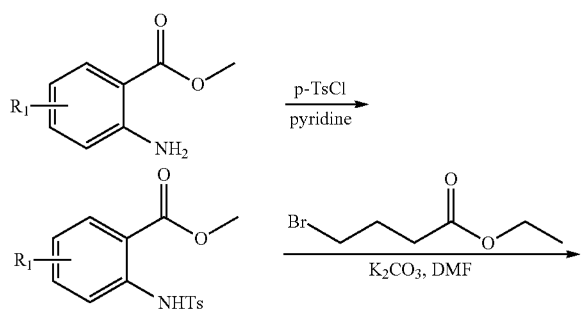

-continued
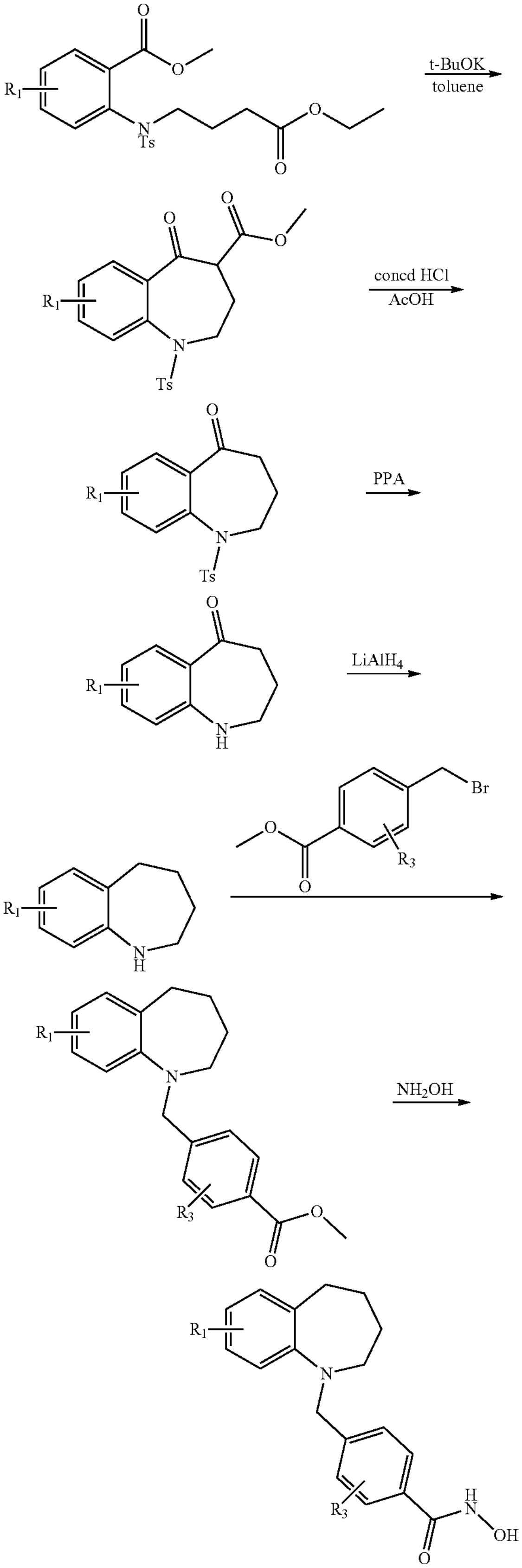
General Method II:
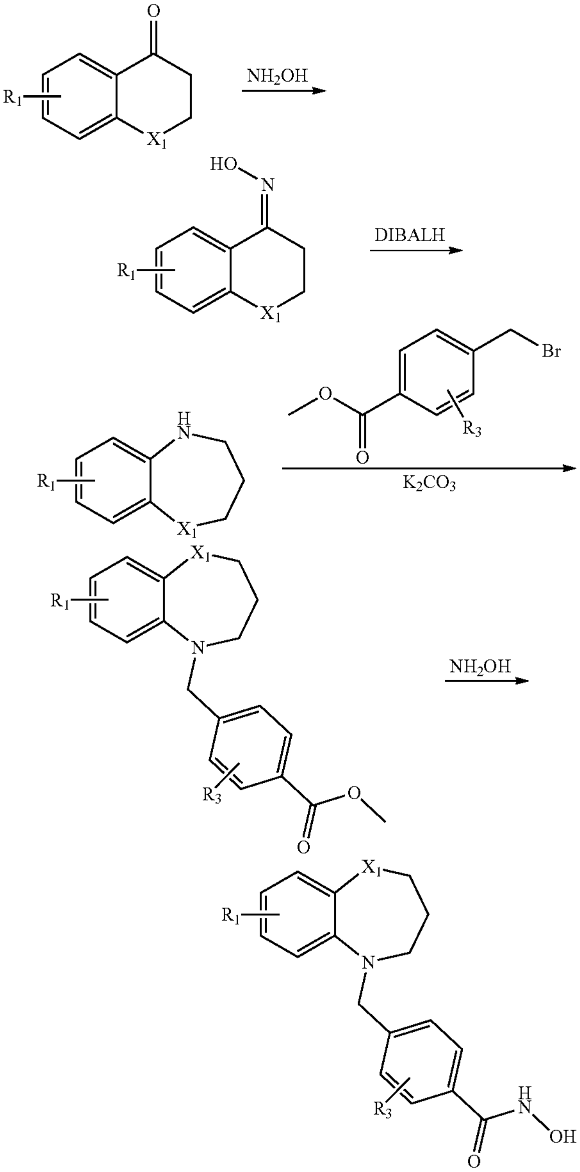
General Method III:
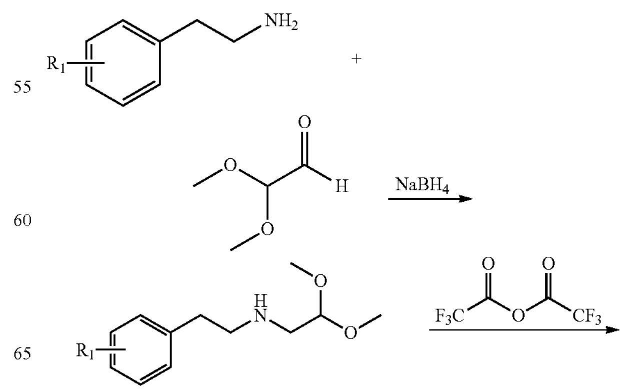

-continued

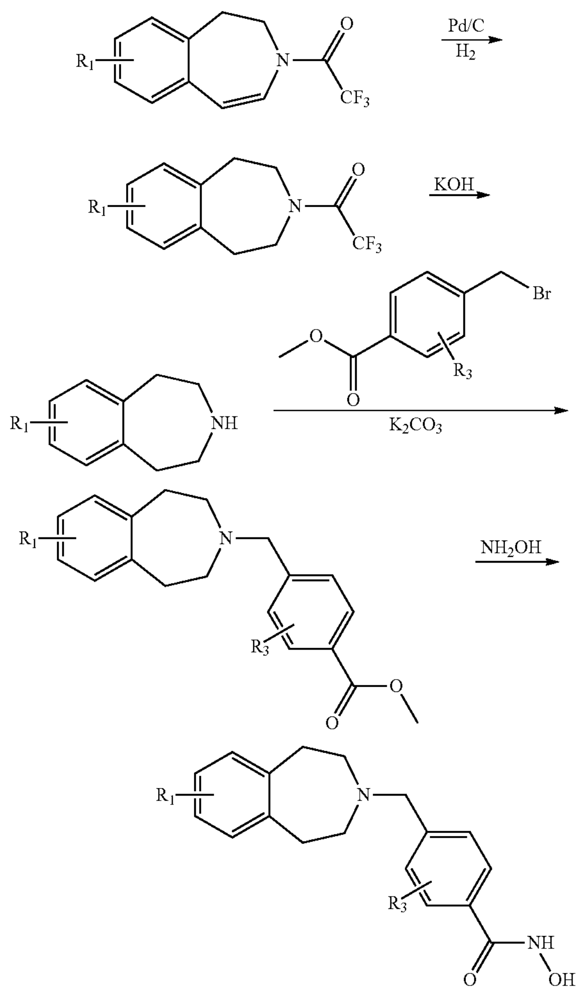

A compound comprising a structure represent by formula I was obtained by the described synthesis general method, which could further react with inorganic acid and organic acid in a solvent, and the corresponding salt of the compound represent by formula I was precipitated by cooling.

The raw materials, compounds and reagents used in the above preparation methods could be purchased through commercial channels.

Embodiment 1: Preparation of 4-((8-chloro-2,3,4,5-tetrahydro-1H-benzo[b]azepin-1-yl)methyl)-N-hydroxybenzamide (T-1)

Prepared according to the synthesis general method I, the synthesis route was as follows:

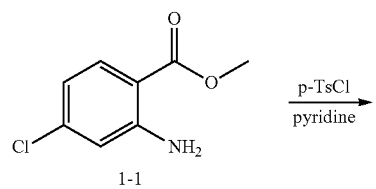

1-1

-continued

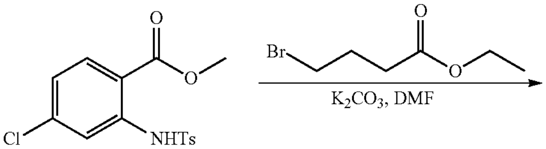
$K_2CO_3$, DMF 1-2

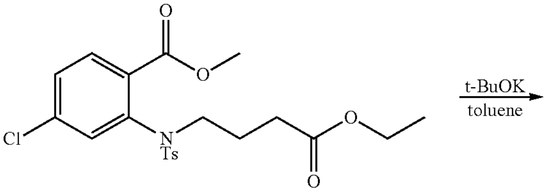
t-BuOK
toluene 1-3

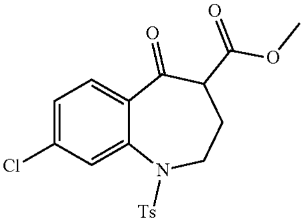

and 1-4

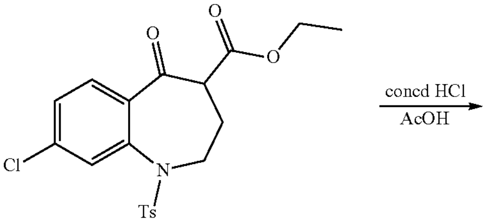
concd HCl
AcOH 1-4′

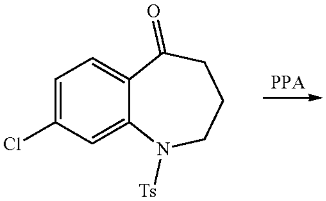
PPA 1-5

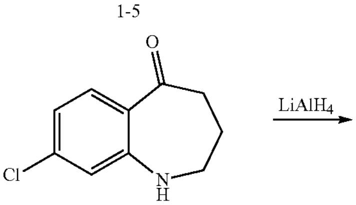
$LiAlH_4$ 1-6

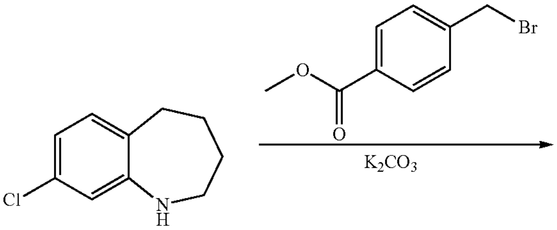
$K_2CO_3$ 1-7

-continued

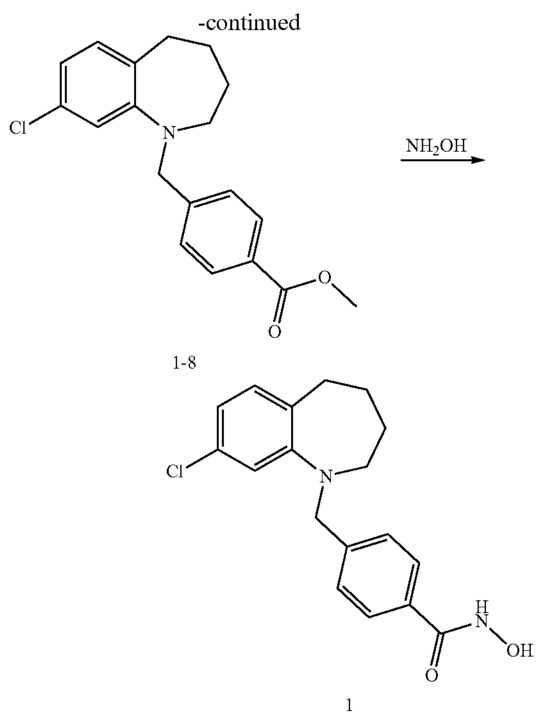

1-8

1

Synthesis of Methyl 4-chloro-2-((4-methylphenyl)sulfonamido)benzoate (1-2)

Methyl 4-chloro-2-aminobenzoate (25 g, 134.69 mmol, 1 eq), p-toluenesulfonyl chloride (30.81 g, 1.2 eq), and pyridine (117.20 g, 11 eq) were sequentially added to a 500 mL three-necked flask, and the reaction was carried out at room temperature for 12 hours. The mixture was filtered to obtain a yellow solid, dissolved to clear with 200 mL of dichloromethane, washed twice with 100 mL of 5% hydrochloric acid and washed once with 100 mL of water; the organic phase was dried and then slurried with 150 mL of 50% ethanol to obtain a white solid with a drying weight of 40.50 g and a yield of 88.49%.

Synthesis of Methyl 4-chloro-2-((N-(4-ethoxy-4-oxobutyl)-4-methylphenyl)sulfonamido)benzoate (1-3)

Intermediate 1-2 (36.40 g, 107.12 mmol, 1 eq) was added to a 1 L three-necked flask, then dissolved in 300 mL of DMF, and then ethyl 4-bromobutyrate (22.98 g, 1.1 eq) and potassium carbonate (41.45 g, 2.8 eq) were added, and the reaction mixture was stirred at 120° C. for 5 hours. The reaction mixture was cooled to room temperature, and 500 mL of water was added thereto, extracted with 500 mL of ethyl acetate; the organic phase was separated and concentrated to dryness, and separated by column chromatography to obtain 35.32 g of white solid with a yield of 72.63%.

Synthesis of Ethyl 8-chloro-5-oxo-1-tosyl-2,3,4,5-tetrahydro-1H-benzo[b]azepine-4-carboxylate (1-4)

Potassium tert-butoxide (16.81 g, 149.80 mmol, 2 eq) and 400 mL of toluene were added to a 1 L three-necked flask, heated to 75° C., and stirred well; intermediate 1-3 (34.00 g, 74.90 mmol, 1eq) was dissolved in 200 mL of toluene, slowly added dropwise to the reaction solution for 1 hour; after the dropwise addition was completed, the reaction solution was heated to 115° C. and refluxed for 1 hour. After cooling to room temperature, the mixture was poured into the ice-water mixture, and the organic phase was separated, and then the aqueous phase was extracted with 200 mL of dichloromethane once. The organic phases were combined, dried over anhydrous sodium sulfate, filtered, and the filtrate was concentrated under reduced pressure to dryness to obtain 32 g of red oil, and directly used in the next step without purification.

Synthesis of 8-chloro-1-tosyl-1,2,3,4-tetrahydro-5H-benzo[b]azepin-5-one (1-5)

32 g of the crude product of intermediate 1-4, 45 mL of concentrated hydrochloric acid, 80 mL of acetic acid, and 10 mL of water were added to a 500 mL three-necked flask, and the mixture was heated to 105° C. and refluxed for 6 hours. After cooling to room temperature, the mixture was poured into ice-water mixture, adjusted to neutral with 10% NaOH, extracted with dichloromethane. The organic phase was dried over anhydrous sodium sulfate, filtered, and the filtrate was concentrated to dryness under reduced pressure, and purified by column chromatography to obtain 16.35 g of colorless oil with a two-step yield of 62.49%.

Synthesis of 8-chloro-1,2,3,4-tetrahydro-5H-benzo[b]azepin-5-one (1-6)

Intermediate 1-5 (8 g, 22.87 mmol) and 60 g of polyphosphoric acid were added to a 250 mL three-necked flask, and the mixture was heated to 90° C. and reacted for 2 hours. The mixture was adjusted to neutral with saturated $NaHCO_3$ solution, extracted with dichloromethane. The organic phase was dried over anhydrous sodium sulfate, filtered, and the filtrate was concentrated to dryness under reduced pressure, and purified by column chromatography to obtain 4.13 g of yellow solid with a yield of 92.31%.

Synthesis of 8-chloro-2,3,4,5-tetrahydro-1H-benzo[b]azepine (1-7)

Intermediate 1-6 (3.00 g, 15.33 mmol, 1 eq) and 50 mL of anhydrous tetrahydrofuran were added to a 100 mL three-necked flask, and the mixture was cooled in an ice-water bath, and then lithium aluminum hydride (1.16 g, 2 eq) was added in portions, and the reaction solution was stirred at room temperature for 2 hours. The reaction solution was slowly poured into the ice-water mixture, stirred for 30 min, filtered with diatomite, and the filtrate was extracted with dichloromethane. The organic phase was dried over anhydrous sodium sulfate, filtered, and the filtrate was concentrated to dryness under reduced pressure, and the purified by column chromatography to obtain 2.15 g of yellow solid with a yield of 77.18%. $^1H$ NMR (400 MHz, DMSO-$d_6$) δ 1.51-1.57 (m, 2H), 1.64-1.70 (m, 2H), 2.61-2.64 (m, 2H), 2.92 (dt, J=5.8, 3.5 Hz, 2H), 5.48 (t, J=3.6 Hz, 1H), 6.67 (dd, J=8.0, 2.2 Hz, 1H), 6.85 (d, J=2.2 Hz, 1H), 7.01 (d, J=8.0 Hz, 1H). ESI-MS(+) m/z=182.00 [M+H]+.

Synthesis of 4-((8-chloro-2,3,4,5-tetrahydro-1H-benzo[b]azepin-1-yl)methyl)benzoate (1-8)

Intermediate 1-7 (2.00 g, 11.01 mmol, 1 eq), methyl 4-(bromomethyl)benzoate (2.52 g, 1 eq), potassium carbonate (2.28 g, 1.5 eq) and 50 mL of DMF were added to a 100 mL three-necked flask, and reacted at 100° C. for 4 hours. The mixture was cooled to room temperature, and 100 mL of water was added, and the mixture was extracted with 100 mL of ethyl acetate. The organic phase was dried, and separated by column chromatography to obtain 2.90 g of white solid with a yield of 79.86%. $^1H$ NMR (400 MHz, DMSO-$d_6$) δ 1.55-1.61 (m, 4H), 2.78-2.81 (m, 2H), 2.89-2.91 (m, 2H), 3.84 (s, 3H), 4.41 (s, 2H), 6.84 (dd, J=8.0, 2.1 Hz, 1H), 6.91 (d, J=2.1 Hz, 1H), 7.11 (d, J=8.0 Hz, 1H), 7.54 (d, J=8.3 Hz, 2H), 7.92-7.95 (m, 2H). ESI-MS(+) m/z=330.10 $[M+H]^+$.

Synthesis of 4-((8-chloro-2,3,4,5-tetrahydro-1H-benzo[b]azepin-1-yl)methyl)-N-hydroxybenzamide (T-1)

20 g of hydroxylamine hydrochloride was dissolved in 200 mL of methanol, and 19 g potassium hydroxide (purity of 85%) was dissolved in 200 mL of methanol, and then the mixture was slowly and evenly mixed in an ice-water bath, stirred at room temperature for 2 hours, and filtered to obtain a filtrate as a hydroxylamine methanol solution. Intermediate 1-8 (2 g, 6.06 mmol) and 50 mL of hydroxylamine methanol solution were added to a 100 mL three-necked flask, and the reaction was carried out at room temperature overnight. The pH was adjusted to neutral with 1 N hydrochloric acid. The mixture was concentrated, followed by addition of ethyl acetate, washed with water to remove hydroxylamine, and the organic phase was dried then concentrated to dryness, and then 20 mL of ethanol/water was added to crystallize, and 1.13 g of white solid was obtained by filtration, and the yield was 56.33%. $^1$H NMR (400 MHz, DMSO-$d_6$) δ 1.53-1.61 (m, 4H), 2.78-2.80 (m, 2H), 2.89 (t, J=4.9 Hz, 2H), 4.36 (s, 2H), 6.83 (dd, J=8.0, 2.1 Hz, 1H), 6.91 (d, J=2.1 Hz, 1H), 7.11 (d, J=7.9 Hz, 1H), 7.45 (d, J=8.0 Hz, 2H), 7.72 (d, J=8.1 Hz, 2H), 10.13 (s, 2H). ESI-MS(+) m/z=331.00 $[M+H]^+$.

Embodiment 2: Preparation of 4-((8-chloro-2,3,4,5-tetrahydro-1H-benzo[b]azepin-1-yl)methyl)-N-hydroxybenzamide (T-2)

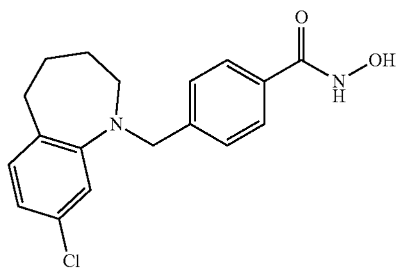 [SMILES: O=C(NO)c1ccc(CN2CCCCc3ccc(Cl)cc32)cc1]

The preparation was carried out according to general method I. White solid, $^1$H NMR (400 MHz, DMSO-$d_6$) δ 1.52-1.60 (m, 4H), 2.79-2.87 (m, 4H), 4.34 (s, 2H), 6.92 (d, J=8.6 Hz, 1H), 7.08 (dd, J=8.5, 2.6 Hz, 1H), 7.17 (d, J=2.6 Hz, 1H), 7.45 (d, J=8.1 Hz, 2H), 7.70-7.72 (m, 2H), 9.04 (s, 1H), 11.18 (s, 1H). ESI-MS(+) m/z=331.00 $[M+H]^+$.

Embodiment 3: Preparation of 4-((8-bromo-2,3,4,5-tetrahydro-1H-benzo[b]azepin-1-yl)methyl)-N-hydroxybenzamide (T-3)

Prepared according to the synthesis general method II, the specific synthesis route was as follows:

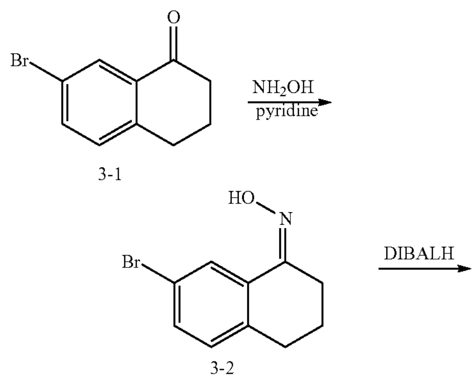

3-1

3-2

-continued

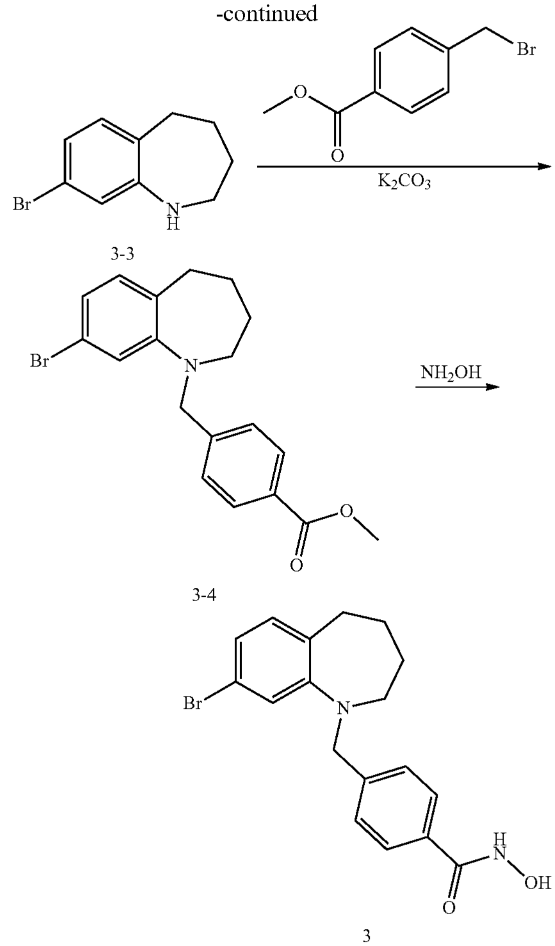

3-3

3-4

3

Synthesis of 7-bromo-3,4-dihydronaphthalen-1(2H)-one oxime (3-2)

7-Bromo-tetralone (10 g, 44.43 mmol, 1 eq), hydroxylamine hydrochloride (6.17 g, 2 eq) and 100 mL of pyridine were added to a 250 mL three-necked flask, and the mixture was stirred at room temperature for 3 hours. The mixture was concentrated and evaporated under reduced pressure to remove pyridine, and 100 mL of water was added thereto. The mixture was extracted with 100 mL of dichloromethane, and the organic phase was separated, dried over anhydrous sodium sulfate, filtered, and the filtrate was concentrated under reduced pressure to dryness, and purified by column chromatography to obtain 9.23 g of white solid with a yield of 86.53%. $^1$H NMR (400 MHz, DMSO-$d_6$) δ 1.71-1.77 (m, 2H), 2.62-2.69 (m, 4H), 7.16 (d, J=8.2 Hz, 1H), 7.42 (dd, J=8.2, 2.2 Hz, 1H), 7.94 (d, J=2.1 Hz, 1H), 11.31 (s, 1H).

Synthesis of 7-bromo-2,3,4,5-tetrahydro-1H-benzo[b]azepine (3-3)

3-2 (9.00 g, 47.06 mmol) and 200 mL of dichloromethane were added to a 250 mL three-necked flask under the protection of nitrogen, and the mixture was cooled down to −5° C., then diisobutylaluminium hydride (DIBALH, 1 M/hexane, 280 mL, 6 eq) was slowly added dropwise for 40 min; after the dropwise addition was completed, the mixture was stirred for 4 hours at room temperature. The reaction was quenched by slowly adding 50 mL of water dropwise, stirred for 1 hour at room temperature, filtered with diatomite, and the filtrate was extracted with dichloromethane. The organic phase was dried over anhydrous sodium sulfate, filtered, and the filtrate was concentrated to dryness under reduced pressure, and then purified by column chromatography to obtain 5.64 g of white solid with a yield of 67.61%. $^1$H NMR (400 MHz, DMSO-$d_6$) δ 1.51-1.57 (m, 2H), 1.63-1.68 (m, 2H), 2.59-2.62 (m, 2H), 2.90-2.93 (m, 2H), 5.49 (t, J=3.6 Hz, 1H), 6.80 (dd, J=8.0, 2.1 Hz, 1H), 6.95 (d, J=8.0 Hz, 1H), 7.00 (d, J=2.1 Hz, 1H).

Synthesis of Methyl 4-((7-bromo-2,3,4,5-tetrahydro-1H-benzo[b]azepin-1-yl)methyl)benzoate (3-4)

Intermediate 3-3 (2.00 g, 11.28 mmol, 1 eq), methyl 4-(bromomethyl)benzoate (2.58 g, 1 eq), potassium carbonate (2.34 g, 1.5 eq) and 50 mL of DMF were added to a 100 mL three-necked flask, and reacted at 100° C. for 4 hours. The mixture was cooled to room temperature, and 100 mL of water was added, and the mixture was extracted with 100 mL of ethyl acetate. The organic phase was dried, and separated by column chromatography to obtain 3.12 g of white solid with a yield of 84.97%. $^1$H NMR (400 MHz, DMSO-$d_6$) δ 1.54-1.60 (m, 4H), 2.77-2.80 (m, 2H), 2.89 (t, J=5.1 Hz, 2H), 3.84 (s, 3H), 4.41 (s, 2H), 6.97 (dd, J=7.9, 2.0 Hz, 1H), 7.03 (d, J=2.0 Hz, 1H), 7.06 (d, J=7.9 Hz, 1H), 7.52-7.55 (m, 2H), 7.93-7.95 (m, 2H).

Synthesis of 4-((7-bromo-2,3,4,5-tetrahydro-1H-benzo[b]azepin-1-yl)methyl)-N-hydroxybenzamide (T-3)

Intermediate 3-4 (2 g, 5.34 mmol) and 50 mL of hydroxylamine methanol solution were added to a 100 mL three-necked flask, and the reaction was carried out at room temperature overnight. The pH was adjusted to neutral with 1 N hydrochloric acid. The mixture was concentrated, followed by addition of ethyl acetate, washed with water to remove hydroxylamine. The organic phase was dried then concentrated to dryness, and 20 mL of ethanol/water was added to crystallize, and 1.27 g of white solid was obtained by filtration, the yield was 63.33%. $^1$H NMR (400 MHz, DMSO-$d_6$) δ 1.52-1.60 (m, 4H), 2.76-2.79 (m, 2H), 2.88 (t, J=4.9 Hz, 2H), 4.36 (s, 2H), 6.97 (dd, J=7.9, 1.9 Hz, 1H), 7.04 (d, J=2.0 Hz, 1H), 7.05 (d, J=8.0 Hz, 1H), 7.45 (d, J=8.2 Hz, 2H), 7.72 (d, J=8.2 Hz, 2H), 9.10 (s, 1H), 11.20 (s, 1H). ESI-MS(+) m/z=375.00 $[M+H]^+$.

Embodiment 4: Preparation of 4-((7-fluoro-2,3,4,5-tetrahydro-1H-benzo[b]azepin-1-yl)methyl)-N-hydroxybenzamide (T-4)

The preparation was carried out according to general method II. $^1$H NMR (400 MHz, DMSO-$d_6$) δ 1.51-1.62 (m, 4H), 2.71-2.79 (m, 2H), 2.88 (t, J=4.9 Hz, 2H), 4.35 (s, 2H), 6.96 (dd, J=7.9, 1.9 Hz, 1H), 7.06 (d, J=2.0 Hz, 1H), 7.03 (d, J=8.0 Hz, 1H), 7.46 (d, J=8.2 Hz, 2H), 7.74 (d, J=8.2 Hz, 2H), 9.12 (s, 1H), 11.21 (s, 1H). ESI-MS(+) m/z=315.00 $[M+H]^+$.

Embodiment 5: Preparation of 4-((7-methoxy-2,3,4,5-tetrahydro-1H-benzo[b]azepin-1-yl)methyl)-N-hydroxybenzamide (T-5)

The preparation was carried out according to general method II. $^1$H NMR (400 MHz, DMSO-$d_6$) δ 1.51-1.58 (m, 4H), 2.73-2.80 (m, 4H), 3.67 (s, 3H), 4.28 (s, 2H), 6.63 (dd, J=8.7, 3.0 Hz, 1H), 6.73 (d, J=3.0 Hz, 1H), 6.89 (d, J=8.7 Hz, 1H), 7.47 (d, J=8.1 Hz, 2H), 7.69-7.71 (m, 2H), 9.06 (s, 1H), 11.16 (s, 1H). ESI-MS(+) m/z=327.14 $[M+H]^+$.

Embodiment 6: Preparation of 4-((8-methoxy-2,3,4,5-tetrahydro-1H-benzo[b]azepin-1-yl)methyl)-N-hydroxybenzamide (T-6)

The preparation was carried out according to general method II. $^1$H NMR (400 MHz, DMSO-$d_6$) δ 1.49-1.60 (m, 4H), 2.72-2.75 (m, 2H), 2.84-2.87 (m, 2H), 3.65 (s, 3H), 4.34 (s, 2H), 6.38 (dd, J=8.2, 2.4 Hz, 1H), 6.47 (d, J=2.5 Hz, 1H), 6.99 (d, J=8.2 Hz, 1H), 7.46 (d, J=8.0 Hz, 2H), 7.70-7.72 (m, 2H), 9.09 (s, 1H), 11.14 (s, 1H). ESI-MS(+) m/z=327.10 $[M+H]^+$.

Embodiment 7: Preparation of 4-((6-methoxy-2,3,4,5-tetrahydro-1H-benzo[b]azepin-1-yl)methyl)-N-hydroxybenzamide (T-7)

The preparation was carried out according to general method II. $^1$H NMR (400 MHz, DMSO-$d_6$) δ 1.47-1.51 (m, 2H), 1.55-1.59 (m, 2H), 2.87 (t, J=5.3 Hz, 4H), 3.73 (s, 3H), 4.34 (s, 2H), 6.57 (dd, J=10.7, 8.2 Hz, 2H), 6.99 (t, J=8.1 Hz, 1H), 7.45 (d, J=7.9 Hz, 2H), 7.71 (d, J=8.0 Hz, 2H), 9.20 (s, 1H), 10.98 (s, 1H). ESI-MS(+) m/z=327.10 $[M+H]^+$.

Embodiment 8: Preparation of 4-((9-methoxy-2,3,4,5-tetrahydro-1H-benzo[b]azepin-1-yl)methyl)-N-hydroxybenzamide (T-8)

The preparation was carried out according to general method II. $^1$H NMR (400 MHz, DMSO-$d_6$) δ 1.47-1.51 (m, 2H), 1.55-1.59 (m, 2H), 2.87 (t, J=5.3 Hz, 4H), 3.73 (s, 3H), 4.34 (s, 2H), 6.57 (dd, J=10.7, 8.2 Hz, 2H), 6.99 (t, J=8.1 Hz, 1H), 7.45 (d, J=7.9 Hz, 2H), 7.71 (d, J=8.0 Hz, 2H), 9.20 (s, 1H), 10.98 (s, 1H). ESI-MS(+) m/z=327.10 $[M+H]^+$.

Embodiment 9: Preparation of 4-((7,8-dimethoxy-2,3,4,5-tetrahydro-1H-benzo[b]azepin-1-yl)methyl)-N-hydroxybenzamide (T-9)

The preparation was carried out according to general method II. $^1$H NMR (400 MHz, DMSO-$d_6$) δ 1.63-1.80 (m, 4H), 2.84 (td, J=6.9, 1.0 Hz, 4H), 3.83 (d, J=7.1 Hz, 6H), 4.43 (t, J=1.0 Hz, 2H), 6.43 (s, 1H), 6.68 (t, J=0.9 Hz, 1H), 7.30 (dt, J=7.4, 1.0 Hz, 2H), 7.85-7.91 (m, 2H), 9.25 (s, 1H), 11.09 (s, 1H). ESI-MS(+) m/z=357.20 $[M+H]^+$.

Embodiment 10: Preparation of 4-((8-phenyl-2,3,4,5-tetrahydro-1H-benzo[b]azepin-1-yl)methyl)-N-hydroxybenzamide (T-10)

The preparation was carried out according to general method II. $^1$H NMR (400 MHz, DMSO-$d_6$) δ 1.53-1.60 (m, 4H), 2.83 (dt, J=19.4, 4.8 Hz, 4H), 4.35 (s, 2H), 6.89 (d, J=1.5 Hz, 1H), 7.17 (dt, J=7.7, 1.0 Hz, 1H), 7.32-7.41 (m, 4H), 7.42-7.49 (m, 2H), 7.52-7.58 (m, 2H), 7.85-7.91 (m, 2H), 9.04 (s, 1H), 11.15 (s, 1H). ESI-MS(+) m/z=373.25 $[M+H]^+$.

Embodiment 11: Preparation of 4-((8-(pyridin-4-yl)-2,3,4,5-tetrahydro-1H-benzo[b]azepin-1-yl)methyl)-N-hydroxybenzamide (T-11)

The preparation was carried out according to general method II. $^1$H NMR (400 MHz, DMSO-$d_6$) δ 1.53-1.60 (m, 4H), 2.83 (dt, J=19.4, 4.8 Hz, 4H), 4.35 (s, 2H), 7.02 (d, J=7.5 Hz, 1H), 7.21 (q, J=1.2 Hz, 1H), 7.35 (dt, J=7.5, 1.1 Hz, 2H), 7.49 (dd, J=7.5, 1.5 Hz, 1H), 7.64-7.70 (m, 2H), 7.85-7.91 (m, 2H), 8.76-8.81 (m, 2H), 9.04 (s, 1H), 11.15 (s, 1H). ESI-MS(+) m/z=374.25 $[M+H]^+$.

Embodiment 12: Preparation of 4-((8-cyclopropyl-2,3,4,5-tetrahydro-1H-benzo[b]azepin-1-yl)methyl)-N-hydroxybenzamide (T-12)

The preparation was carried out according to general method II. $^1$H NMR (600 MHz, DMSO-$d_6$) δ 0.55 (dt, J=6.5, 3.2 Hz, 2H), 0.78-0.91 (m, 2H), 1.42-1.66 (m, 4H), 2.78 (dt, J=41.5, 5.1 Hz, 4H), 4.34 (s, 2H), 6.50 (dd, J=7.6, 1.8 Hz, 1H), 6.64 (d, J=1.9 Hz, 1H), 6.95 (d, J=7.7 Hz, 1H), 7.47 (d, J=8.0 Hz, 2H), 7.71 (d, J=8.0 Hz, 2H), 9.03 (s, 1H), 11.16 (s, 1H). ESI-MS(+) m/z=337.19 $[M+H]^+$.

Embodiment 13: Preparation of 4-((8-dimethylamino-2,3,4,5-tetrahydro-1H-benzo[b]azepin-1-yl) methyl)-N-hydroxybenzamide (T-13)

The preparation was carried out according to general method II. $^1$H NMR (400 MHz, DMSO-$d_6$) δ 1.64 (pd, J=7.1, 0.9 Hz, 2H), 1.76 (pd, J=7.0, 0.8 Hz, 2H), 2.75 (td, J=7.0, 1.0 Hz, 2H), 2.95 (s, 6H), 3.35 (t, J=7.0 Hz, 2H), 4.43 (t, J=1.0 Hz, 2H), 6.14 (d, J=1.5 Hz, 1H), 6.47 (dd, J=7.5, 1.5 Hz, 1H), 6.99 (dt, J=7.5, 1.1 Hz, 1H), 7.31 (dt, J=7.5, 1.1 Hz, 2H), 7.84-7.90 (m, 2H), 9.26 (s, 1H), 10.96 (s, 1H). ESI-MS(+) m/z=340.20 $[M+H]^+$.

Embodiment 14: Preparation of 4-((8-(piperidin-1-yl)-2,3,4,5-tetrahydro-1H-benzo[b]azepin-1-yl) methyl)-N-hydroxybenzamide (T-14)

The preparation was carried out according to general method II. $^1$H NMR (400 MHz, DMSO-$d_6$) δ 1.58-1.81 (m, 10H), 2.77 (td, J=7.0, 1.0 Hz, 2H), 3.34 (t, J=7.0 Hz, 2H), 3.43 (t, J=7.0 Hz, 4H), 4.43 (t, J=1.0 Hz, 2H), 6.14 (d, J=1.5 Hz, 1H), 6.54 (dd, J=7.5, 1.5 Hz, 1H), 7.06 (dt, J=7.5, 1.1 Hz, 1H), 7.34 (dt, J=7.6, 1.0 Hz, 2H), 7.86-7.92 (m, 2H), 9.26 (s, 1H), 10.96 (s, 1H). ESI-MS(+) m/z=380.25 $[M+H]^+$.

Embodiment 15: Preparation of 4-((3,4-dihydrobenzo[b][1,4]oxazepin-5(2H)-yl)methyl)-N-hydroxybenzamide (15)

The preparation was carried out according to general method II. $^1$H NMR (400 MHz, DMSO-$d_6$) δ 1.90 (p, J=5.8 Hz, 2H), 3.19-3.22 (m, 2H), 4.09 (t, J=5.8 Hz, 2H), 4.44 (s, 2H), 6.68-6.73 (m, 1H), 6.77-6.79 (m, 1H), 6.82-6.85 (m, 2H), 7.41 (d, J=8.1 Hz, 2H), 7.72 (d, J=8.0 Hz, 2H), 9.26 (s, 1H), 10.96 (s, 1H). ESI-MS(+) m/z=299.09 $[M+H]^+$.

Embodiment 16: Preparation of 4-((3,4-dihydrobenzo[b][1,4]thiazepin-5(2H)-yl)methyl)-N-hydroxybenzamide (T-16)

The preparation was carried out according to general method II. $^1$H NMR (400 MHz, DMSO-$d_6$) δ 1.85 (t, J=5.8 Hz, 2H), 2.92 (t, J=5.8 Hz, 2H), 3.28 (t, J=5.4 Hz, 2H), 4.45 (s, 2H), 6.76 (t, J=7.4 Hz, 1H), 6.88 (d, J=8.0 Hz, 1H), 7.03-7.08 (m, 1H), 7.26 (dd, J=7.7, 1.6 Hz, 1H), 7.43 (d, J=7.9 Hz, 2H), 7.71 (d, J=7.9 Hz, 2H), 9.11 (s, 1H), 11.10 (s, 1H). ESI-MS(+) m/z=315.10 $[M+H]^+$.

Embodiment 17: Preparation of 4-((5-methyl-2,3,4,5-tetrahydro-1H-benzo[b][1.4]diazepin-1-yl)methyl-N-hydroxybenzamide (T-17)

The preparation was carried out according to general method II. $^1$H NMR (400 MHz, DMSO-$d_6$) δ 1.96 (dp, J=28.4, 7.1 Hz, 2H), 2.96 (s, 3H), 3.36 (t, J=7.1 Hz, 2H), 3.44 (t, J=7.1 Hz, 2H), 4.41 (s, 2H), 6.76 (t, J=7.4 Hz, 1H), 6.88 (d, J=8.0 Hz, 1H), 7.03-7.08 (m, 1H), 7.26 (dd, J=7.7, 1.6 Hz, 1H), 7.43 (d, J=7.9 Hz, 2H), 7.71 (d, J=7.9 Hz, 2H), 9.15 (s, 1H), 11.16 (s, 1H). ESI-MS(+) m/z=312.20 $[M+H]^+$.

Embodiment 18: Preparation of 4-((5-oxo-2,3,4,5-tetrahydro-1H-benzo[b]azepin-1-yl)methyl)-N-hydroxybenzamide (T-18)

The preparation was carried out according to general method II. $^1$H NMR (400 MHz, DMSO-$d_6$) δ 1.91 (p, J=7.1 Hz, 2H), 2.62-2.68 (m, 2H), 3.43 (t, J=7.1 Hz, 2H), 4.47 (t, J=1.0 Hz, 2H), 6.89 (dd, J=7.4, 1.6 Hz, 1H), 7.28-7.35 (m, 3H), 7.39 (td, J=7.5, 1.6 Hz, 1H), 7.59 (dd, J=7.4, 1.6 Hz, 1H), 7.84-7.89 (m, 2H), 9.11 (s, 1H), 11.10 (s, 1H). ESI-MS(+) m/z=311.15 $[M+H]^+$.

Embodiment 19: Preparation of 4-((5-hydroxy-2,3,4,5-tetrahydro-1H-benzo[b]azepin-1-yl)methyl)-N-hydroxybenzamide (T-19)

The preparation was carried out according to general method II. $^1$H NMR (400 MHz, DMSO-$d_6$) δ 1.75-1.81 (m, 1H), 1.81-1.89 (m, 3H), 3.34-3.42 (m, 2H), 3.51 (d, J=7.5 Hz, 1H), 4.43 (t, J=1.0 Hz, 2H), 4.74-4.82 (m, 1H), 6.72 (dd, J=7.5, 1.5 Hz, 1H), 6.83 (td, J=7.5, 1.5 Hz, 1H), 7.08 (td, J=7.5, 1.6 Hz, 1H), 7.32 (dddd, J=13.5, 7.5, 1.8, 0.8 Hz, 3H), 7.84-7.89 (m, 2H), 9.11 (s, 1H), 11.10 (s, 1H). ESI-MS(+) m/z=313.20 $[M+H]^+$.

Embodiment 20: Preparation of 4-((5-hydroxy-2,3,4,5-tetrahydro-1H-benzo[b]azepin-1-yl)methyl)-N-hydroxybenzamide (T-20)

The preparation was carried out according to general method II. $^1$H NMR (400 MHz, DMSO-$d_6$) δ 1.78-2.03 (m, 4H), 3.23 (d, J=1.5 Hz, 3H), 3.36 (t, J=6.9 Hz, 2H), 4.36 (dt, J =12.3, 0.9 Hz, 1H), 4.51 (dt, J=12.5, 1.1 Hz, 1H), 4.61 (ddt, J=7.4, 5.8, 1.1 Hz, 1H), 6.72 (dd, J=7.5, 1.5 Hz, 1H), 6.83 (td, J=7.5, 1.5 Hz, 1H), 7.08 (td, J=7.5, 1.6 Hz, 1H), 7.32 (dddd, J=13.5, 7.5, 1.8, 0.8 Hz, 3H), 7.84-7.89 (m, 2H), 9.11 (s, 1H), 11.10 (s, 1H). ESI-MS(+) m/z=327.30 $[M+H]^+$.

Embodiment 21: Preparation of 4-((5-dimethylamino-2,3,4,5-tetrahydro-1H-benzo[b]azepin-1-yl) methyl)-N-hydroxybenzamide (T-21)

The preparation was carried out according to general method II. $^1$H NMR (400 MHz, DMSO-$d_6$) δ 1.77-1.91 (m, 4H), 2.31 (d, J=1.5 Hz, 6H), 3.28-3.37 (m, 2H), 3.65-3.72 (m, 1H), 4.43 (t, J=1.0 Hz, 2H), 6.67 (dd, J=7.5, 1.5 Hz, 1H), 6.75 (td, J=7.5, 1.5 Hz, 1H), 7.04 (td, J=7.5, 1.6 Hz, 1H), 7.31 (dt, J=7.5, 1.1 Hz, 2H), 7.36-7.42 (m, 1H), 7.84-7.90 (m, 2H), 9.26 (s, 1H), 10.96 (s, 1H). ESI-MS(+) m/z=340.20 $[M+H]^+$.

Embodiment 22: Preparation of 4-((2,3,4,5-tetrahydro-1H-benzo[b]azepin-1-yl)fluoromethyl)-N-hydroxybenzamide (T-22)

The preparation was carried out according to general method II. $^1$H NMR (400 MHz, DMSO-$d_6$) δ 1.53-1.60 (m, 4H), 2.83 (dt, J=19.4, 4.8 Hz, 4H), 5.85 (s, 1H), 6.81 (t, J=7.3 Hz, 1H), 6.94 (d, J=8.0 Hz, 1H), 7.06 (td, J=7.7, 1.7 Hz, 1H), 7.10 (d, J=7.1 Hz, 1H), 7.47 (d, J=8.0 Hz, 2H), 7.71 (d, J=7.9 Hz, 2H), 9.04 (s, 1H), 11.15 (s, 1H). ESI-MS(+) m/z=315.20 $[M+H]^+$.

Embodiment 23: Preparation of 4-((2,3,4,5-tetrahydro-1H-benzo[b]azepin-1-yl)difluoromethyl)-N-hydroxybenzamide (T-23)

The preparation was carried out according to general method II. $^1$H NMR (600 MHz, DMSO-$d_6$) δ 1.53-1.60 (m, 4H), 2.83 (dt, J=19.4, 4.8 Hz, 4H), 6.81 (t, J=7.3 Hz, 1H), 6.94 (d, J=8.0 Hz, 1H), 7.06 (td, J=7.7, 1.7 Hz, 1H), 7.10 (d, J=7.1 Hz, 1H), 7.47 (d, J=8.0 Hz, 2H), 7.71 (d, J=7.9 Hz, 2H), 9.04 (s, 1H), 11.15 (s, 1H). ESI-MS(+) m/z=333.20 $[M+H]^+$.

Embodiment 24: Preparation of 4-((2,3,4,5-tetrahydro-1H-benzo[b]azepin-1-yl)methyl)-2-fluoro-N-hydroxybenzamide (T-24)

The preparation was carried out according to general method II. $^1H$ NMR (400 MHz, DMSO-$d_6$) δ 1.65 (pd, J=7.1, 0.9 Hz, 2H), 1.77 (pd, J=6.9, 0.8 Hz, 2H), 2.78 (td, J=7.1, 1.0 Hz, 2H), 3.33 (t, J=7.1 Hz, 2H), 4.42 (dt, J=12.3, 1.0 Hz, 1H), 4.51 (dt, J=12.5, 0.9 Hz, 1H), 6.52 (dd, J=7.4, 1.5 Hz, 1H), 6.64 (td, J=7.5, 1.5 Hz, 1H), 6.84 (dq, J=7.5, 1.1 Hz, 1H), 6.95 (td, J=7.4, 1.6 Hz, 1H), 7.14 (tt, J=8.0, 1.3 Hz, 2H), 7.79 (dd, J=7.4, 5.0 Hz, 1H), 8.82 (d, J=4.9 Hz, 1H), 9.09 (s, 1H), 11.25 (s, 1H). ESI-MS(+) m/z=315.20 $[M+H]^+$.

Embodiment 25: Preparation of 4-((7-methoxy-1,2,4,5-tetrahydro-3H-benzo[d]azepin-3-yl)methyl)-N-hydroxybenzamide (T-25)

The preparation was carried out according to general method III, and the synthetic route was as follows:

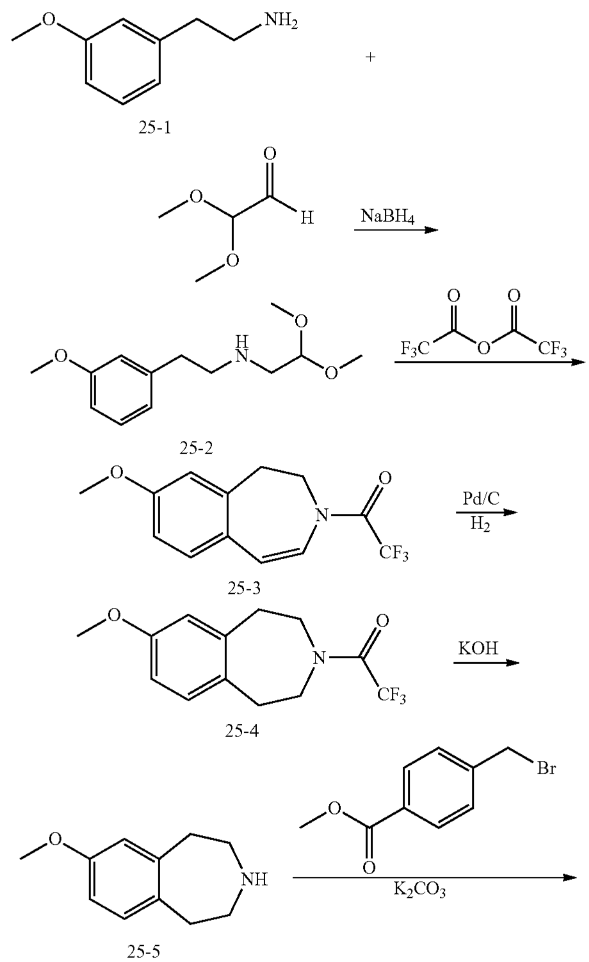

25-1

25-2

25-3

25-4

25-5

-continued

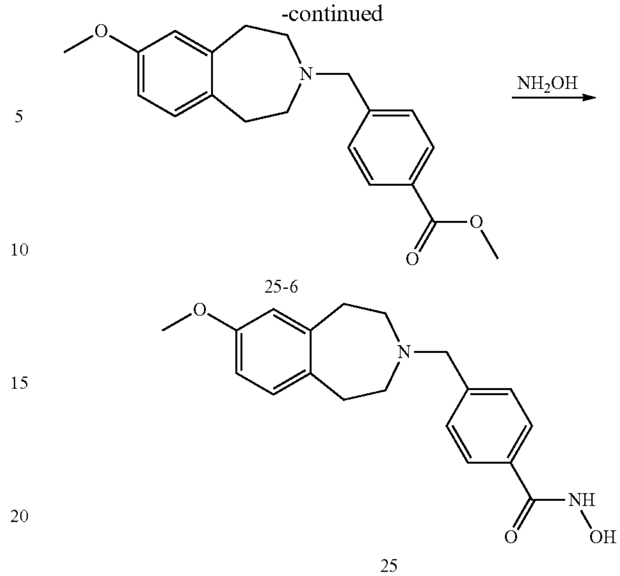

25-6

25

The product was a white solid, $^1H$ NMR (400 MHz, DMSO-$d_6$) δ 2.49 (s, 2H), 2.53 (s, 2H), 2.78 (dd, J=6.3, 3.8 Hz, 2H), 2.81 (dd, J=6.2, 3.7 Hz, 2H), 3.62 (s, 2H), 3.69 (s, 3H), 6.63 (dd, J=8.2, 2.7 Hz, 1H), 6.69 (d, J=2.7 Hz, 1H), 6.99 (d, J=8.2 Hz, 1H), 7.41 (d, J=8.0 Hz, 2H), 7.65-7.81 (m, 2H), 9.09 (s, 1H), 11.25 (s, 1H). ESI-MS(+) m/z=327.15 $[M+H]^+$.

Embodiment 26: Preparation of 4-((6-methoxy-1,2,4,5-tetrahydro-3H-benzo[d]azepin-3-yl)methyl)-N-hydroxybenzamide (T-26)

The preparation was carried out according to general method III. $^1H$ NMR (400 MHz, DMSO-$d_6$) δ 2.48 (m, 4H), 2.83 (m, 2H), 2.93 (m, 2H), 3.60 (s, 2H), 6.65-6.74 (m, 1H), 6.76-6.83 (m, 1H), 7.04 (m, 1H), 7.40 (d, J=8.0 Hz, 2H), 7.68-7.80 (m, 2H), 9.11 (s, 1H), 11.25 (s, 1H). ESI-MS(+) m/z=327.15 $[M+H]^+$.

Embodiment 27: Preparation of 4-((6-bromo-9-methoxy-1,2,4,5-tetrahydro-3H-benzo[d]azepin-3-yl)methyl)-N-hydroxybenzamide (T-27)

The preparation was carried out according to general method III. $^1H$ NMR (400 MHz, DMSO-$d_6$) δ 2.46-2.50 (m, 2H), 2.97-3.00 (m, 2H), 3.08-3.11 (m, 2H), 3.59 (s, 2H), 3.74 (s, 3H), 6.79 (d, J=8.9 Hz, 1H), 7.36-7.39 (m, 3H), 7.73 (d, J=8.0 Hz, 2H), 9.09 (s, 1H), 11.20 (s, 1H). ESI-MS(+) m/z=405.13 $[M+H]^+$.

Embodiment 28: Preparation of 4-((6-cyclopropyl-9-methoxy-1,2,4,5-tetrahydro-3H-benzo[d]azepin-3-yl)methyl)-N-hydroxybenzamide (T-28)

The preparation was carried out according to general method III. $^1H$ NMR (400 MHz, DMSO-$d_6$) δ 0.37-0.51 (m, 2H), 0.73-0.89 (m, 2H), 1.79 (tt, J=8.4, 5.4 Hz, 1H), 2.47 (q, J =4.7 Hz, 4H), 2.94 (dd, J=7.0, 3.1 Hz, 2H), 3.11 (dd, J=6.8, 3.1 Hz, 2H), 3.58 (s, 2H), 3.69 (s, 3H), 6.69 (d, J=8.5 Hz, 1H), 6.87 (d, J=8.5 Hz, 1H), 7.40 (d, J=8.0 Hz, 2H), 7.63-7.82 (m, 2H), 9.08 (s, 1H), 11.20 (s, 1H). ESI-MS(+) m/z=366.88 $[M+H]^+$.

Embodiment 29 Inhibitory Activity of Compounds Against HDAC

The in vitro inhibitory activity of histone deacetylase of the compound was determined according to the instructions of HDAC1 and HDAC6 inhibitor screening kit (Biovision Company). HDAC6 inhibitor Rocilinostat (ACY 1215)

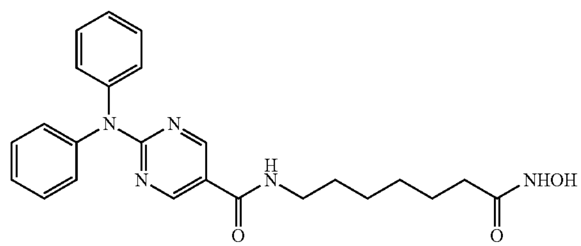

in the clinical stage and compound SW-100 were used as positive controls.

The experimental results are shown in the table:

| | $IC_{50}$ (nM) | |
|---|---|---|
| Compd. | HDAC6 | HDAC1 |
| Rocilinostat (ACY-1215) | 6.8 | 19 |
| SW-100 | 2.4 | 69 |
| T-1 | 37 | >500 |
| T-2 | 14 | 406 |
| T-3 | 43 | 400 |
| T-4 | 8.2 | 414 |
| T-5 | 5.6 | 257 |
| T-6 | 8.2 | 294 |
| T-7 | 6.5 | 277 |
| T-8 | 9.2 | 287 |
| T-9 | 8.6 | 269 |
| T-10 | 129 | >500 |
| T-11 | 14.3 | >500 |
| T-12 | 45 | >500 |
| T-13 | 85 | >500 |
| T-14 | 142 | >500 |
| T-15 | 6.2 | 367 |
| T-16 | 1.2 | 254 |
| T-17 | 7.4 | >500 |
| T-18 | 7.2 | 421 |
| T-19 | 6.4 | 442 |
| T-24 | 12 | >500 |
| T-25 | 17 | >500 |
| T-26 | 97 | >500 |
| T-27 | 29 | 431 |
| T-28 | 22 | >500 |

It can be seen from the above table that the compounds of the present disclosure show better inhibitory activity against HDAC6 (most $IC_{50}$<100 nM), and some compounds have comparable or better inhibitory activity to the positive controls Rocilinostat (ACY-1215) and SW-100. In addition, the inhibitory activity $IC_{50}$ against HDAC1 are all >250 nM; compared with HDAC1, the compounds of the present disclosure can selectively inhibit HDAC6, most of the selectivity are >30 times, or even 50 times, and the selectivity is better than Rocilinostat and SW-100.

Embodiment 30 In Vitro Anti-Proliferative Activity Test on Tumor Cells and Human Normal Cells The anti-proliferative activities of some compounds of the present disclosure under the condition of single concentration (10 μM) on glioma cell line U-87MG, myeloma cell line RPMI 8226, human liver cancer cell line HepG2, human lung cancer cell line A549 and MRC-5 human normal embryo lung fibroblast were measured, and Rocilinostat (ACY-1215) was selected as a control. The specific results are shown in the table (unit: Inh % in 10 μM).

Test method: The tumor cells in the logarithmic growth phase with good growth status were inoculated into 96-well plates at $4\times10^3$ per well, and 8 duplicate wells were set up in each group. The cells were cultured in a cell incubator, after the cells adhered to the wall, the corresponding plasmids were transfected. After 48 hours of continuous culture, the drug-containing culture medium was discarded, 10 μL of freshly prepared toxicity detection solution CCK8 was added to each well, and the mixture was placed and cultured in an incubator for 4 hours, and the OD value was measured at a wavelength of 450 nm with a microplate reader. The experiment was repeated 3 times, and the average of the experimental results was taken as the final experimental result, and the inhibition rate was calculated.

| Compound | U-87MG (Glioma) | RPMI 8226 (Myeloma) | Hep G2 (Liver cancer) | A549 (Lung cancer) | MRC-5 (Normal cell line) |
|---|---|---|---|---|---|
| Ricolinostat | 42.1 | 99.3 | 93.4 | 51.6 | 46.7 |
| T-2 | B | A | A | C | E |
| T-5 | B | A | A | C | E |
| T-15 | B | A | A | D | E |
| T-16 | A | A | A | C | E |
| T-19 | A | A | A | D | E |
| T-21 | B | A | A | C | E |
| T-28 | B | A | A | D | E |

A 100≥ to >90;
B: 80< to ≤90;
C: 70< to ≤80;
D: 50< to ≤70
E: <50

It can be seen from the above table that, compared with the positive control Rocilinostat, the compound of the present disclosure has good in vitro anti-tumor cell proliferation activity for various tumor cells, and has higher inhibitory activity for glioma cell line U-87MG, myeloma cell line RPMI 8226 and human liver cancer cell line HepG2, the anti-tumor cell proliferation activity of some compounds is better than that of positive control drugs.

At the same time, compared with Rocilinostat, the compound of the present disclosure has weaker inhibitory activity on MRC-5 human normal embryo lung fibroblasts and lower toxic and side effects, which reveals that the compound of the present disclosure has better selectivity in inhibiting the proliferation of tumor cells and normal cells, and indicates that it may have lower toxic and side effects when used as an anti-tumor drug.

Embodiment 31 Protective Effect of Compounds on HCA-Induced Neuronal Cell Damage HCA (5 mmol/L) was used to induce the injury of mixed cells and primary neurons in rat cortex, and the effects of different concentrations (test concentration: 0.1 μM, 1.0 μM and 10.0 μM) of the compound on the injury were observed, and the activity, quantity, morphology and necrosis of neurons and glial cells were detected, and the effect of compounds on normal neurons was observed; Tubastatin A, a similar HDAC6 inhibitor compound with neuroprotective effect, was used as a control. The results show that the compounds of the present disclosure have a certain protective effect against HCA-induced neuronal excitotoxicity.

Among them, the in vitro activity of compounds T-2, T-5, T-15, T-16, T-19, T-21 and T-28 is stronger than that of the HDAC6 inhibitor compound Tubastatin A with neuroprotective effect at the same dose, and shows a certain dose-effect relationship, suggesting that the compound of the present disclosure has neuroprotective effect and can be used for the treatment of neurodegenerative-related diseases. The results are as shown in FIG. 1.

Embodiment 32 Experiment of the Effect of Compounds on hERG Potassium Channel Whole-cell patch clamp technique was used to record the changes of hERG current (IKr) after different concentrations of compounds acted on HEK293 cells (hERG-HEK293 steady-state cells) expressing hERG potassium channels to study the half inhibitory concentration ($IC_{50}$) of the above compounds on IKr.

The potential cardiac toxicity and side effects in vitro of some compounds T-2, T-5, T-15, T-16, T-19, T-21 and T-28 of the present disclosure were preliminarily investigated. The experimental results are as follows:

| Compd | hERG $IC_{50}$ (μM) |
|---|---|
| T-2 | >10 |
| T-5 | >10 |
| T-15 | >10 |
| T-16 | >10 |
| T-19 | >10 |
| T-21 | >10 |
| T-28 | >10 |

The results of the hERG experiment shows that the inhibitory activities of the test compounds T-2, T-5, T-15, T-16, T-19, T-21 and T-28 on hERG potassium channels are all greater than 10 μM, suggesting that the potential cardiotoxicity of the compounds of the present disclosure is low.

Embodiment 33 Toxicity Test of Maximum Tolerance Dose of Compound by Intragastric Administration 40 ICR mice, half male and half male, weighing 18 to 20 g, were divided into 4 groups with 10 animals in each group. After 6 hours of fasting, the test samples in each group were taken with sterilized plastic syringe and orally gavaged at a volume of 0.3 mL/10 g. The general physical signs of animals and the death of animals were recorded at 1, 2 and 4 hours after administration. The animals were observed for 14 consecutive days after administration, and the body weights and physical signs and death were observed and recorded daily. The dead animals were dissected to observe whether there were any visible pathological changes in the organs of the animals, and pathological examinations were carried out on suspicious tissues and organs.

The experimental results show that the maximum tolerated doses of the compounds T-2, T-5, T-15, T-16, T-19, T-21 and T-28 of the present disclosure to mice by intragastric administration are greater than 1000 mg/kg, and the tolerance of animals is better.

Embodiment 34 PK Test of Compounds

Some of compounds T-2, T-5, T-15, T-16, T-19, T-21 and T-28 of the present disclosure were administered to male SD rats by single intraperitoneal administration, and the drug concentrations of the compounds in rat brain and plasma were determined by LC-MS/MS method, and the brain/plasma drug concentration ratio of the test compound t=1.0 h was calculated to evaluate the brain permeability of the active compound. With compound SW-100 as the control, the test results are as shown in the table:

| Compound | Blood-brain barrier permeability (B/P) |
|---|---|
| II-ING-39 | 0.77 |
| SW-100 | 1.82 |
| T-2 | >2.0 |
| T-5 | >2.0 |
| T-15 | >2.0 |
| T-16 | >2.0 |
| T-19 | >2.0 |
| T-21 | >2.0 |
| T-28 | >2.0 |

The test results show that compared with the positive controls II-ING-39 and SW-100, the compounds of the present disclosure show better blood-brain permeability.

Although the specific embodiments of the present disclosure have been described above, those skilled in the art should understand that these are only examples, and various changes or modifications can be made to these embodiments without departing from the principle and essence of the present disclosure. Accordingly, the scope of protection of the present disclosure is defined by the claims.

What is claimed is:

1. A benzonitric heterocyclic compound represented by formula I-1 or a pharmaceutically acceptable salt thereof,

I-1

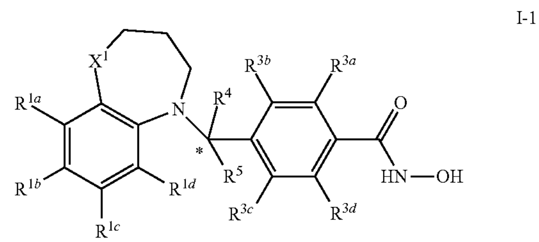

$X^1$ is

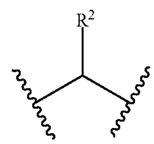

$R^2$ is independently hydrogen, hydroxyl, $C_1$-$C_4$ alkyl, $C_1$-$C_4$ alkyl-O—, $(R^aR^b)N$— or O═;

$R^{1a}$, $R^{1b}$, $R^{1c}$ and $R^{1d}$ are independently hydrogen, halogen, hydroxyl, cyano or $R^1$-L-;

-L- is independently a linker bond, —($C_1$-$C_4$ alkyl)-, —O—, —C(═O)— or —S(═O)$_2$—;

$R^1$ is independently $C_1$-$C_6$ alkyl, $C_3$-$C_7$ cycloalkyl, $C_6$-$C_{10}$ aryl, $(R^cR^d)N$—, 3- to 7-membered heterocycloalkyl or 5- to 10-membered heteroaryl, or, the $C_1$-$C_6$ alkyl, $C_3$-$C_7$ cycloalkyl, $C_6$-$C_{10}$ aryl, $(R^cR^d)N$—, 3- to 7-membered heterocycloalkyl and 5- to 10-membered heteroaryl are substituted by one or more substituents of $R^e$; in the 3- to 7-membered heterocycloalkyl and the 3- to 7-membered heterocycloalkyl substituted by one or more substituents of $R^e$, the heteroatom is selected from one or more of N, O, S, S(═O) and $S(═O)_2$, and the number of heteroatoms is 1 to 3; in the 5- to 10-membered heteroaryl and the 5- to 10-membered heteroaryl substituted by one or more substituents of $R^e$, the heteroatom is selected from one or more of N, O and S, and the number of heteroatoms is 1 to 4; $R^e$ is independently hydroxyl, halogen, cyano or $C_1$-$C_4$ alkyl; when there are multiple substituents, they are the same or different;

$R^a$, $R^b$, $R^c$ and $R^d$ are independently hydrogen or $C_1$-$C_4$ alkyl;

$R^{3a}$, $R^{3b}$, $R^{3c}$, $R^{3d}$, $R^4$ and $R^5$ are independently hydrogen, halogen, $C_1$-$C_4$ alkyl or $C_1$-$C_4$ alkyl substituted by one or more halogen; when there are multiple substituents, they are the same or different;

a carbon atom with "*" indicates that when it is a chiral carbon atom, it is a S configuration, R configuration or a mixture thereof.

2. The benzonitric heterocyclic compound represented by formula I-1 or the pharmaceutically acceptable salt thereof according to claim 1, wherein, when $R^2$ is independently $C_1$-$C_4$ alkyl or $C_1$-$C_4$ alkyl-O—, the $C_1$-$C_4$ alkyl in the $C_1$-$C_4$ alkyl and $C_1$-$C_4$ alkyl-O— is methyl, ethyl, n-propyl, isopropyl, n-butyl, isobutyl, sec-butyl or tert-butyl;

or, when $R^{1a}$, $R^{1b}$, $R^{1c}$ and $R^{1d}$ are independently halogen, the halogen is fluorine, chlorine, bromine or iodine;

or, when -L- is independently —($C_1$-$C_4$ alkyl)-, the —($C_1$-$C_4$ alkyl)- is methylene, ethylene, propylene, butylene, isopropylidene, isobutylene, sec-butylene or tert-butylene;

or, when $R^1$ is independently $C_1$-$C_6$ alkyl, $C_1$-$C_6$ alkyl substituted by one or more substituents of $R^e$, the $C_1$-$C_6$ alkyl in the $C_1$-$C_6$ alkyl and $C_1$-$C_6$ alkyl substituted by one or more substituents of $R^e$ is independently methyl, ethyl, n-propyl, isopropyl, n-butyl, isobutyl, sec-butyl or tert-butyl;

or when $R^1$ is independently $C_3$-$C_7$ cycloalkyl, $C_3$-$C_7$ cycloalkyl substituted by one or more substituents of $R^e$, the $C_3$-$C_7$ cycloalkyl in the $C_3$-$C_7$ cycloalkyl and $C_3$-$C_7$ cycloalkyl substituted by one or more substituents of $R^e$ is independently cyclopropyl, cyclobutyl, cyclopentyl, cyclohexyl and cycloheptyl;

or, when $R^1$ is independently $C_6$-$C_{10}$ aryl, $C_6$-$C_{10}$ aryl substituted by one or more substituents of $R^e$, the $C_6$-$C_{10}$ aryl in the $C_6$-$C_{10}$ aryl and $C_6$-$C_{10}$ aryl substituted with one or more substituents of $R^e$ is independently phenyl or naphthyl;

or, when $R^1$ is independently 3- to 7-membered heterocycloalkyl and 3- to 7-membered heterocycloalkyl substituted by one or more substituents of $R^e$, the 3- to 7-membered heterocycloalkyl in the 3- to 7-membered heterocycloalkyl and 3- to 7-membered heterocycloalkyl substituted by one or more substituents of $R^e$ is independently 5- to 6-membered heterocycloalkyl, wherein the heteroatom is selected from one or more of N, O and S, and the number of heteroatoms is 1 to 2;

or, when $R^1$ is independently 5- to 10-membered heteroaryl and 5- to 10-membered heteroaryl substituted by one or more substituents of $R^e$, the 5- to 10-membered heteroaryl in the 5- to 10-membered heteroaryl and 5- to 10-membered heteroaryl substituted by one or more substituents of $R^e$ is independently 5- to 6-membered heteroaryl, wherein the heteroatom is selected from one or more of N, O and S, and the number of heteroatoms is 1 to 2;

or, when $R^e$ is independently halogen, the halogen is fluorine, chlorine, bromine or iodine;

or, when $R^e$ is independently $C_1$-$C_4$ alkyl, the $C_1$-$C_4$ alkyl is methyl, ethyl, n-propyl, isopropyl, n-butyl, isobutyl, sec-butyl or tert-butyl;

or, when $R^a$, $R^b$, $R^c$ and $R^d$ are independently $C_1$-$C_4$ alkyl, the $C_1$-$C_4$ alkyl is methyl, ethyl, n-propyl, isopropyl, n-butyl, isobutyl, sec-butyl or tert-butyl;

or, when $R^{3a}$, $R^{3b}$, $R^{3c}$, $R^{3d}$, $R^4$ and $R^5$ are independently $C_1$-$C_4$ alkyl or $C_1$-$C_4$ alkyl substituted by one or more halogen, the $C_1$-$C_4$ alkyl in the $C_1$-$C_4$ alkyl or $C_1$-$C_4$ alkyl substituted by one or more halogen is methyl, ethyl, n-propyl, isopropyl, n-butyl, isobutyl, sec-butyl or tert-butyl;

or, when $R^{3a}$, $R^{3b}$, $R^{3c}$, $R^{3d}$, $R^4$ and $R^5$ are independently halogen or $C_1$-$C_4$ alkyl substituted by one or more halogen, the halogen in the halogen or $C_1$-$C_4$ alkyl substituted by one or more halogen is fluorine, chlorine, bromine or iodine;

or, when $R^1$ is independently $C_1$-$C_6$ alkyl, $C_3$-$C_7$ cycloalkyl, $C_6$-$C_{10}$ aryl, $(R^cR^d)N$—, 3- to 7-membered heterocycloalkyl or 5- to 10-membered heteroaryl, and the $C_1$-$C_6$ alkyl, $C_3$-$C_7$ cycloalkyl, $C_6$-$C_{10}$ aryl, $(R^cR^d)N$—, 3- to 7-membered heterocycloalkyl and 5- to 10-membered heteroaryl are substituted by substituents of $R^e$, and the $R^e$ is independently halogen, and the number of $R^e$ is 1, 2 or 3;

or, when $R^{3a}$, $R^{3b}$, $R^{3c}$, $R^{3d}$, $R^4$ and $R^5$ are independently $C_1$-$C_4$ alkyl substituted by one or more halogen, the number of halogen substitutions is substituted by 1 to 3 halogens.

3. The benzonitric heterocyclic compound represented by formula I-1 or the pharmaceutically acceptable salt thereof according to claim 1, wherein, $R^2$ is independently hydrogen, hydroxyl, $C_1$-$C_4$ alkyl, $(R^aR^b)N$— or O═;

or, -L- is independently a linker bond or —O—;

or, $R^1$ is independently $C_1$-$C_6$ alkyl, $C_3$-$C_7$ cycloalkyl, $C_6$-$C_{10}$ aryl, $(R^cR^d)N$—, 3- to 7-membered heterocycloalkyl, or 5- to 10-membered heteroaryl;

or, $R^1$-L- is $C_3$-$C_7$ cycloalkyl, $C_6$-$C_{10}$ aryl, $(R^cR^d)N$—, 3- to 7-membered heterocycloalkyl, 5- to 10-membered heteroaryl or $C_1$-$C_6$ alkyl-O—;

or, $R^{1a}$, $R^{1b}$, $R^{1c}$ and $R^{1d}$ are independently hydrogen, halogen or $R^1$-L-;

or, $R^4$ and $R^5$ are independently hydrogen or halogen;

or, $R^a$, $R^b$, $R^c$ and $R^d$ are independently $C_1$-$C_4$ alkyl;

or, $R^{3a}$, $R^{3b}$, $R^{3c}$ and $R^{3d}$ are independently hydrogen or halogen.

4. The benzonitric heterocyclic compound represented by formula I-1 or the pharmaceutically acceptable salt thereof according to claim 1, wherein, $R^{1a}$, $R^{1b}$, $R^{1c}$ and $R^{1d}$ are independently hydrogen, fluorine, chlorine, bromine, methoxy, cyclopropyl, phenyl,

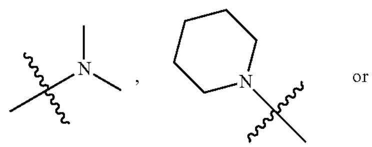

or

-continued

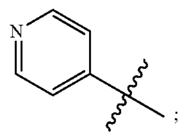

or, $R^2$ is independently hydrogen, hydroxyl, methyl, methoxy,

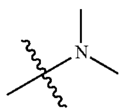 [SMILES: *N(C)C]

or O═;

or, $R^4$ and $R^5$ are independently hydrogen or fluorine;

or, $R^{3a}$, $R^{3b}$, $R^{3c}$ and $R^{3d}$ are independently hydrogen or fluorine.

5. The benzonitric heterocyclic compound represented by formula I-1 or the pharmaceutically acceptable salt thereof according to claim 1, wherein, the benzonitric heterocyclic compound represented b formula I-1 is selected from any of the following structures:

T-1

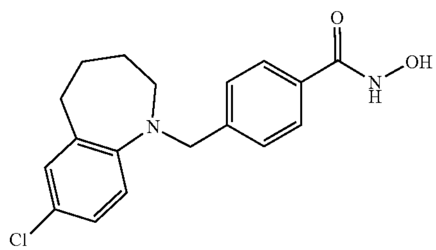

T-2

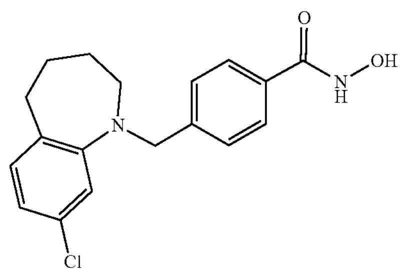

T-3

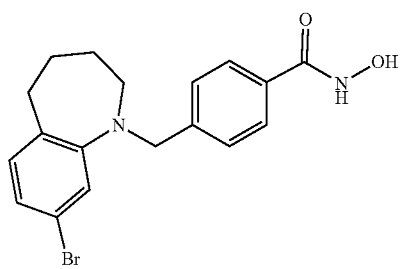

-continued

T-4

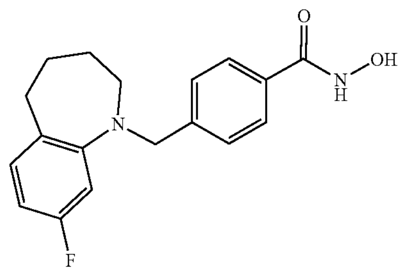

T-5

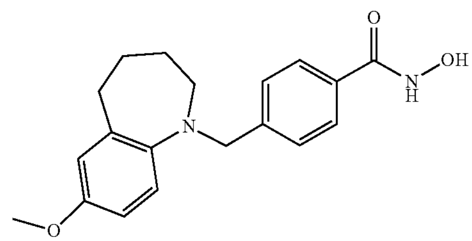

T-6

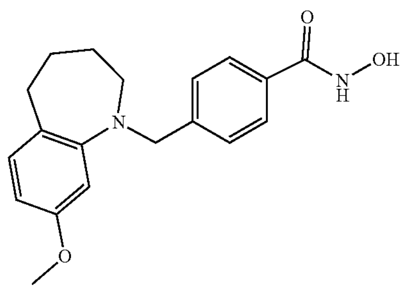

T-7

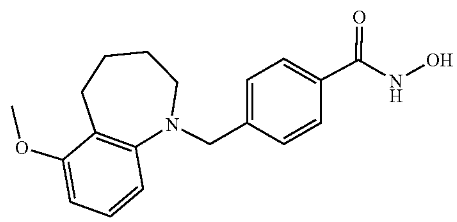

T-8

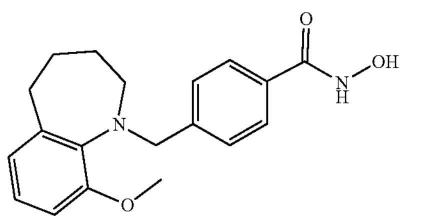

T-9

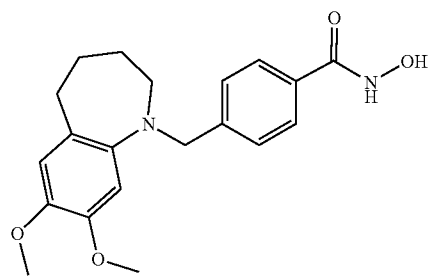

-continued
T-10
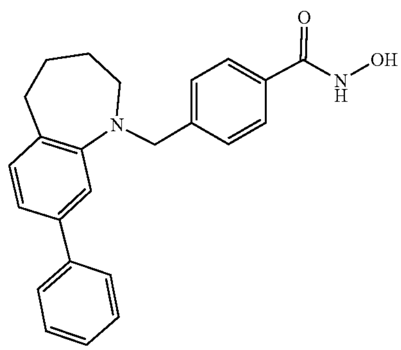
T-11
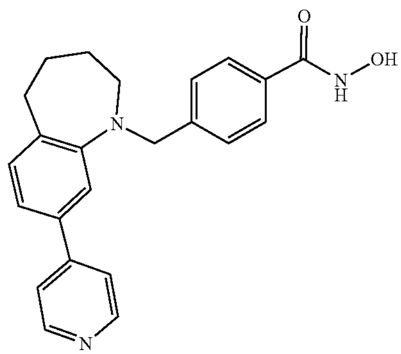
T-12
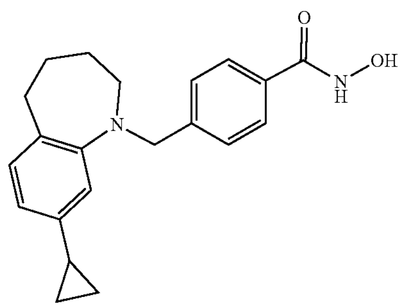
T-13
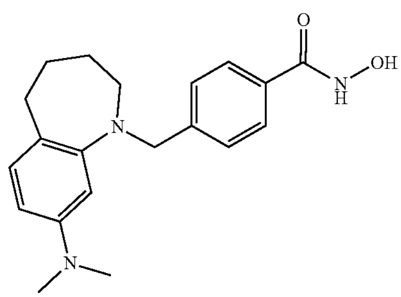
T-14
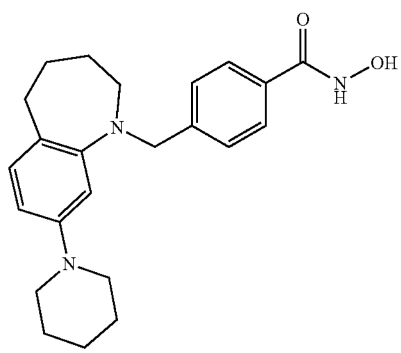
-continued
T-18
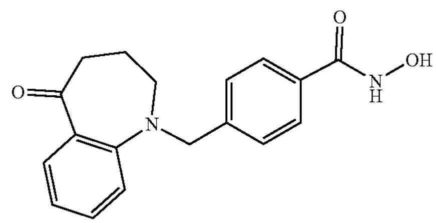
T-19
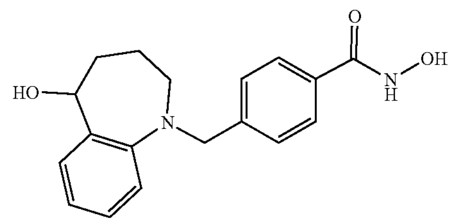
T-20
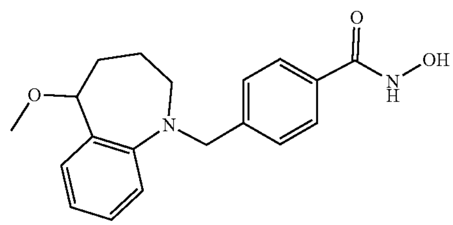
T-21
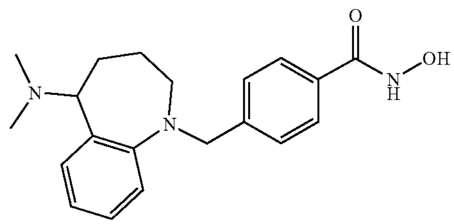
T-22
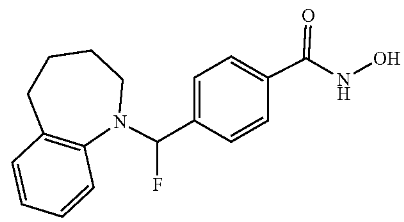
T-23
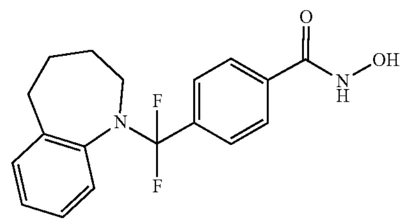
T-24
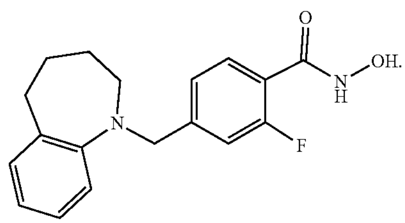

6. A pharmaceutical composition, comprising the benzonitric heterocyclic compound represented by formula I-1 or the pharmaceutically acceptable salt thereof as defined in claim 1, and one or more pharmaceutically acceptable carriers.

7. A method of inhibiting HDAC in a subject in need thereof, comprising administering the benzonitric heterocyclic compound represented by formula I-1 or the pharmaceutically acceptable salt thereof as defined in claim 1 into the subject.

8. The benzonitric heterocyclic compound represented by formula I-1 or the pharmaceutically acceptable salt thereof according to claim 2, wherein, $R^2$ is independently $C_1$-$C_4$ alkyl or $C_1$-$C_4$ alkyl-O—, the $C_1$-$C_4$ alkyl in the $C_1$-$C_4$ alkyl and $C_1$-$C_4$ alkyl-O— is methyl;

or, when $R^{1a}$, $R^{1b}$, $R^{1c}$ and $R^{1d}$ are independently halogen, the halogen is fluorine, chlorine or bromine;

or, when $R^1$ is independently $C_1$-$C_6$ alkyl, $C_1$-$C_6$ alkyl substituted by one or more substituents of $R^e$, the $C_1$-$C_6$ alkyl in the $C_1$-$C_6$ alkyl and $C_1$-$C_6$ alkyl substituted by one or more substituents of $R^e$ is independently methyl;

or, when $R^1$ is independently $C_3$-$C_7$ cycloalkyl, $C_3$-$C_7$ cycloalkyl substituted by one or more substituents of $R^e$, the $C_3$-$C_7$ cycloalkyl in the $C_3$-$C_7$ cycloalkyl and $C_3$-$C_7$ cycloalkyl substituted by one or more substituents of $R^e$ is independently cyclopropyl;

or, when $R^1$ is independently $C_6$-$C_{10}$ aryl, $C_6$-$C_{10}$ aryl substituted by one or more substituents of $R^e$, the $C_6$-$C_{10}$ aryl in the $C_6$-$C_{10}$ aryl and $C_6$-$C_{10}$ aryl substituted with one or more substituents of $R^e$ is independently phenyl;

or, when $R^1$ is independently 3- to 7-membered heterocycloalkyl and 3- to 7-membered heterocycloalkyl substituted by one or more substituents of $R^e$, the 3- to 7-membered heterocycloalkyl in the 3- to 7-membered heterocycloalkyl and 3- to 7-membered heterocycloalkyl substituted by one or more substituents of $R^e$ is independently piperidinyl;

or, when $R^1$ is independently 5- to 10-membered heteroaryl and 5- to 10-membered heteroaryl substituted by one or more substituents of $R^e$, the 5- to 10-membered heteroaryl in the 5- to 10-membered heteroaryl and 5- to 10-membered heteroaryl substituted by one or more substituents of $R^e$ is independently pyridyl;

or, when $R^e$ is independently $C_1$-$C_4$ alkyl, the $C_1$-$C_4$ alkyl is methyl;

or, when $R^a$, $R^b$, $R^c$ and $R^d$ are independently $C_1$-$C_4$ alkyl, the $C_1$-$C_4$ alkyl is methyl;

or, when $R^{3a}$, $R^{3b}$, $R^{3c}$, $R^{3d}$, $R^4$ and $R^5$ are independently $C_1$-$C_4$ alkyl or $C_1$-$C_4$ alkyl substituted by one or more halogen, the $C_1$-$C_4$ alkyl in the $C_1$-$C_4$ alkyl or $C_1$-$C_4$ alkyl substituted by one or more halogen is methyl.

9. The benzonitric heterocyclic compound represented by formula I-1 or the pharmaceutically acceptable salt thereof according to claim 3, wherein, $R^2$ is independently hydrogen, hydroxyl, $C_1$-$C_4$ alkyl or O═;

or, $R^1$ is independently $C_1$-$C_6$ alkyl;

or, $R^1$-L- is $C_1$-$C_6$ alkyl-O;

or, one or two of $R^{1a}$, $R^{1b}$, $R^{1c}$ and $R^{1d}$ are independently halogen or $R^1$-L-, the rest are hydrogen;

or, $R^4$ and $R^5$ are independently hydrogen;

or, $R^{3a}$ is hydrogen or halogen; $R^{3b}$, $R^{3c}$ and $R^{3d}$ are independently hydrogen.

10. The method according to claim 7, wherein, the HDAC is HDAC6.

11. A method of treating cancer or nervous diseases, comprising administering the benzonitric heterocyclic compound represented by formula I-1 or the pharmaceutically acceptable salt thereof as defined in claim 1 into the subject, wherein the cancers are selected from the group consisting of ovarian cancer, breast cancer, liver cancer, prostate cancer, lung cancer, glioblastoma, and myeloma; and the nervous diseases are selected from the group consisting of Parkinson's disease, Huntington's disease, and amyotrophic lateral sclerosis.

12. A method of inhibiting HDAC in a subject in need thereof, comprising administering the pharmaceutical composition as defined in claim 6 into the subject.

13. A method of treating cancer or nervous diseases, comprising administering the pharmaceutical composition as defined in claim 6 into the subject, wherein the cancers are selected from the group consisting of ovarian cancer, breast cancer, liver cancer, prostate cancer, lung cancer, glioblastoma, and myeloma; and the nervous diseases are selected from the group consisting of Parkinson's disease, Huntington's disease, and amyotrophic lateral sclerosis.

* * * * *